US012728114B2

(12) United States Patent
Steiner et al.

(10) Patent No.: US 12,728,114 B2
(45) Date of Patent: Sep. 8, 2026

(54) METHODS OF TREATING INFLAMMATION

(71) Applicant: VERU INC., Miami, FL (US)

(72) Inventors: Mitchell S. Steiner, Germantown, TN (US); Kester Gary Barnette, Wake Forest, NC (US)

(73) Assignee: VERU INC., Miami, FL (US)

( * ) Notice: Subject to any disclaimer, the term of this patent is extended or adjusted under 35 U.S.C. 154(b) by 360 days.

(21) Appl. No.: 18/552,799

(22) PCT Filed: Aug. 4, 2021

(86) PCT No.: PCT/US2021/044572

§ 371 (c)(1),
(2) Date: Sep. 27, 2023

(87) PCT Pub. No.: WO2022/216308

PCT Pub. Date: Oct. 13, 2022

(65) Prior Publication Data

US 2024/0180879 A1 Jun. 6, 2024

Related U.S. Application Data

(60) Provisional application No. 63/171,013, filed on Apr. 5, 2021.

(51) Int. Cl.
*A61K 31/4178* (2006.01)
*A61P 29/00* (2006.01)

(52) U.S. Cl.
CPC .......... *A61K 31/4178* (2013.01); *A61P 29/00* (2018.01)

(58) Field of Classification Search
CPC ............ A61K 31/4178; A61K 31/4174; A61K 31/426; A61K 31/427; A61P 29/00; A61P 31/00; A61P 31/14
See application file for complete search history.

(56) References Cited

U.S. PATENT DOCUMENTS

2019/0374512 A1 12/2019 Li et al.
2019/0389841 A1 12/2019 Li et al.
2020/0024270 A1 1/2020 Li et al.
2021/0308105 A1 10/2021 Steiner et al.

FOREIGN PATENT DOCUMENTS

WO WO-2006/084338 8/2006
WO WO-2019/222385 11/2019
WO WO-2019222385 A1 * 11/2019 ........... C07D 403/04
WO WO-2021/203100 10/2021

OTHER PUBLICATIONS

CAS Registry No. 1332881-26-1 (which entered the STN database on Sep. 20, 2011). (Year: 2011).*
Dutton, Gail; "Veru's Compound Shows Promise as Antiviral/Anti-Inflammatory Therapeutic for COVID-19", BioSpace 2020, para1-4 (retrieved on Oct. 18, 2021 from https://www.biospace.com/article/veryu-s-lead-compound-shows-promise-as-antiviral-anti-inflammatory-therapeutic-for-covid-10); p. 1 p. 2 p. 3.
Leal, Maria C. et al; "Interleukin-1β and tumor necrosis factor-α: reliable targets for protective therapies in Parkinson's Disease?", Frontiers in Cellular Neuroscience 2013, vol. 7, Article 53, pp. 1-10.
International Search Report dated Nov. 15, 2021 in respect of PCT Int'l Application No. PCT/US21/44572.
Mahmud, F., et al., "Orally available tubulin inhibitor VERU-111 enhances antitumor efficacy in paclitaxel-resistant lung cancer", Cancer Letters 2020, vol. 495, pp. 76-88, doi: 10.1016/j.canlet.2020.09.004.
Naaz, Fatima et al., "1,2,3-triazole tethered Indole-3-glyoxamide derivatives as multiple inhibitors of 5-LOX, COX-2 & Tubulin: Their anti-proliferative & anti-inflammatory activity", Bioorganic Chemistry 2018, vol. 81, pp. 1-20.
Zhang, Ling-Hua et al., "The Synthetic Compound CC-5079 Is a Potent Inhibitor of Tubulin Polymerization and Tumor Necrosis Factor-a Production with Antitumor Activity", Cancer Res 2006; vol. 66, No. 2, pp. 951-959.
Iwasaki, Masae et al., "Inflammation Triggered by SARS-CoV-2 and ACE2 Augment Drives Multiple Organ Failure of Severe COVID-19: Molecular Mechanisms and Implications", *Inflammation* 2021, vol. 44, No. 1, DOI: 10.1007/sl0753-020-01337-3.
Schlesinger, Naomi et al; "Colchicine in COVID-19: an Old Drug, New Use", Current Pharmacology Reports 2020, 6: 137-145; DOI: 10.1007/s40495-020-00225-6.

* cited by examiner

*Primary Examiner* — Kamal A Saeed
*Assistant Examiner* — Meghan C Heasley
(74) *Attorney, Agent, or Firm* — Mark S. Cohen; PEARL COHEN LLP

(57) ABSTRACT

The present invention relates to methods of treating inflammation using compounds that disrupt the cytoskeleton by causing microtubule depolymerization and preventing or reducing the assembly of activated inflammasomes.

21 Claims, 5 Drawing Sheets

METHODS OF TREATING INFLAMMATION

CROSS-REFERENCE TO RELATED APPLICATIONS

This application is a U.S. national stage application under 35 U.S.C. 371 of PCT International Application No. PCT/US2021/044572, filed Aug. 4, 2021, which claims priority to U.S. Provisional Application No. 63/171,013, filed Apr. 5, 2021, each of which is hereby incorporated by reference in its entirety.

FIELD OF THE INVENTION

The present invention is directed to methods of treating inflammation using compounds having cytoskeleton disruptor activity, and formulations including said compounds with pharmaceutical acceptable excipients and/or additional cytoskeleton disruptor compounds.

BACKGROUND OF THE INVENTION

Inflammation is the immune system's response to harmful stimuli, such as pathogens, damaged cells, toxic compounds, or irradiation and acts by removing injurious stimuli and initiating the healing process. Inflammation is therefore a defense mechanism that is vital to health. Usually, during acute inflammatory responses, cellular and molecular events and interactions efficiently minimize impending injury or infection. This mitigation process contributes to restoration of tissue homeostasis and resolution of the acute inflammation. However, uncontrolled acute inflammation can contribute to a variety of serious human inflammatory diseases such as, but not limited to, gout, arthritis, Alzheimer's disease, reaction to viral infections, allergies, asthma, autoimmune diseases, neurodegenerative diseases, Parkinson's disease, coeliac disease, glomerulonephritis, cardiovascular disease, hepatitis, inflammatory bowel disease, fatty liver disease, atherosclerosis, type 2 diabetes, cancer, obesity, endometriosis, and many others.

At the tissue level, inflammation is characterized by redness, swelling, heat, pain, and loss of tissue function, which result from local immune, vascular and inflammatory cell responses to infection or injury. Important microcirculatory events that occur during the inflammatory process include vascular permeability changes, leukocyte recruitment and accumulation, and inflammatory mediator release.

Various pathogenic factors, such as infection, tissue injury, or cardiac infarction, can induce inflammation by causing tissue damage. The etiologies of inflammation can be infectious or non-infectious. In response to tissue injury, the body initiates a chemical signaling cascade that stimulates responses aimed at healing affected tissues. These signals activate leukocyte chemotaxis from the general circulation to sites of damage. These activated leukocytes produce cytokines that induce inflammatory responses.

Central to the host defense innate response process is the inflammasome, a multiprotein intracellular complex that detects environmental irritants, monosodium urate crystals, cholesterol crystals, islet amyloid polypeptides, pathogenic microbes and viruses (e.g., coronaviruses) resulting in the activation of highly proinflammatory cytokines, interleukin-1beta (IL-1β) and IL-18. Inflammasomes also induce a form of cell death termed pyroptosis. The inflammasome complex includes, Nod-like receptors (NLRs) and AIM2, the adaptor apoptosis associated speck-like (ASC) protein, and caspase-1. An example is NLRP3 (aka NALP3 or cryopyrin) which is a member of the NLR family. NLRP3 inflammasome assembly and activation is mediated by microtubules. Microtubules actively transport ASC on the mitochondria to the perinuclear region to colocalize together with NLRP3 on the endoplasmic reticulum. Once inflammasome assembly is completed, caspase-1 processes pro-IL1-β into activated IL1-β and IL-18 which initiates the immune over-reaction leading to the inflammatory cascade, tissue damage, and inflammatory disease.

Microtubules are cytoskeletal filaments consisting of α- and β-tubulin heterodimers and are involved in a wide range of cellular functions, including shape maintenance, vesicle transport, cell motility, and division. Tubulin is the major structural component of the microtubules and a verified target for a variety of anticancer drugs. Compounds that are able to interfere with microtubule-tubulin equilibrium in cells can be effective in reducing inflammation. Other compounds that interfere with microtubule-tubulin equilibrium in cells, such as paclitaxel and vinblastine, are limited by their toxicity.

Drugs that target the cytoskeleton, especially the microtubule components, are important therapeutic agents for cancer and inflammation. The clinical activity of these compounds is dictated by the location that these compounds bind on the α and β-tubulin heterodimers that compose the microtubule filament. Three major binding sites on α and β-tubulin subunits have been identified as taxanes-, vinca alkaloid-, and colchicine-binding sites. Such drugs are commonly classified into two major categories: microtubule-stabilizing (e.g., taxanes) and microtubule-destabilizing or depolymerizing agents (e.g., vinca alkaloids and colchicine).

Colchicine has a narrow therapeutic index with no clear distinction between nontoxic, toxic, and lethal doses. Metabolically, colchicine is eliminated via P-glycoprotein (P-gp; also known as Multi-Drug Resistance 1 (MDR1) protein). Drug-drug interactions are common with CYP3A4 and P-glycoprotein inhibitors which can increase colchicine blood concentrations to toxic levels leading to colchicine poisoning and death. Life-threatening and fatal toxicities have been observed when colchicine is administered with P-gp or strong CYP3A4 inhibitors even at approved therapeutic doses. Additional serious toxicities including myelosuppression, disseminated intravascular coagulation, and cell damage in renal, hepatic, circulatory, and central nervous systems have been observed with approved therapeutic doses of colchicine. These observed serious adverse events limit the clinical use of colchicine.

A major problem with taxanes, as with many biologically active natural products, is its lipophilicity and lack of solubility in aqueous systems. This leads to the use of emulsifiers like Cremophor EL and Tween 80 in clinical preparations, which leads to serious hypersensitivity reactions.

Nocodazole is a synthetic compound identified in a screen for anthelminthic agents. Nocodazole is a microtubule depolymerization agent as it binds to free tubulin heterodimers and prevents them from incorporating into microtubules. It has not been used clinically because of poor bioavailability and high toxicity.

The cellular and viral solution to master intracellular trafficking is an organized network or filaments including microtubules. Cells require microtubules for long-term normal physiology, and viruses are obligate intracellular parasites that completely depend on the physiology of the host cell. The inventions of this application address a novel method of treating inflammation using compounds having cytoskeleton disruptor activity and formulations including the compounds with pharmaceutical acceptable excipients and/or additional cytoskeleton disruptor compounds.

SUMMARY OF THE INVENTION

The invention encompasses methods of treating inflammation, using compounds having cytoskeleton disruptor activity, and formulations including the compounds with pharmaceutical acceptable excipients and/or additional cytoskeleton disruptor compounds, in a subject in need thereof by administering to the subject a formulation having a therapeutically effective amount of a compound of Formula (I)

(I)

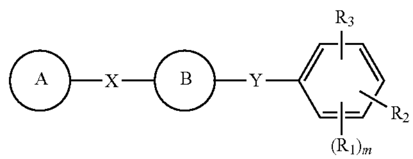

wherein

- A is phenyl, indolyl, or indazolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;
- B is an imidazole or benzimidazole, optionally substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2$CN, hydroxyl, or $NO_2$;
- $R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;
- X is a bond or NH;
- Y is —C═O; and
- m is 1-3, or a pharmaceutically acceptable salt, hydrate, polymorph, or isomer thereof.

In an embodiment of the invention, the method encompasses compounds of Formula I wherein A is phenyl or indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

- B is an imidazole, optionally substituted with at least one of $(C_1-C_4)$alkyl;
- $R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;
- X is a bond or NH;
- Y is —C═O; and
- m is 1-3, or a pharmaceutically acceptable salt, hydrate, polymorph, or isomer thereof.

In another embodiment of the invention, the methods of treating inflammation encompass compounds of Formula I wherein A is phenyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

- B is an imidazole, optionally substituted with at least one of $(C_1-C_4)$alkyl;
- $R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;
- X is a bond or NH;
- Y is —C═O; and
- m is 1-3, or a pharmaceutically acceptable salt, hydrate, polymorph, or isomer thereof.

In yet another embodiment of the invention, the methods of treating inflammation encompass compounds of Formula I wherein A is indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

- B is an imidazole, optionally substituted with at least one of $(C_1-C_4)$alkyl;
- $R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;
- X is a bond or NH;
- Y is —C═O; and
- m is 1-3, or a pharmaceutically acceptable salt, hydrate, polymorph, or isomer thereof.

An embodiment of the invention, the methods of treating inflammation encompass compounds of Formula I wherein A is indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

- B is an imidazole, optionally substituted with at least one of $(C_1-C_4)$alkyl;
- $R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;
- X is a bond;
- Y is —C═O; and
- m is 1-3, or a pharmaceutically acceptable salt, hydrate, polymorph, or isomer thereof.

Another embodiment of the invention encompasses methods of treating inflammation in a subject in need thereof by administering to the subject a formulation having a therapeutically effective amount of a compound of the Formula VII:

(VII)

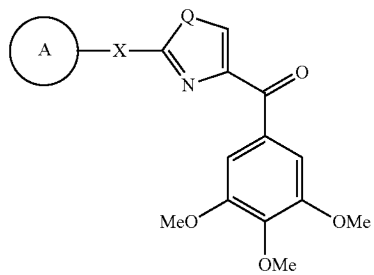

wherein

X is a bond or NH;

Q is NH; and

A is a phenyl, indolyl, or indazolyl ring optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$; or a pharmaceutically acceptable salt, hydrate, polymorph, or isomer thereof. In another embodiment of the invention, the method encompasses compounds of Formula VII wherein X is NH.

In yet another embodiment of the invention, the method encompasses compounds of Formula VII, wherein X is a bond; Q is NH; and A is an indolyl ring optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$; or a pharmaceutically acceptable salt, hydrate, polymorph, or isomer thereof.

An embodiment of the invention encompasses methods of treating inflammation in a subject in need thereof by administering to the subject a formulation having a therapeutically effective amount of a compound of the Formula VII(c):

VII(c)

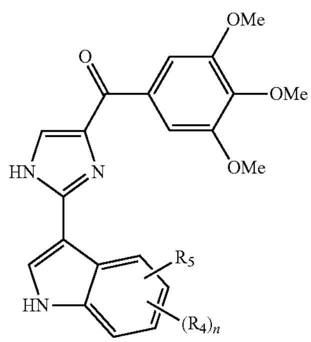

wherein $R_4$ and $R_5$ independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$; and n is 1-4; or a pharmaceutically acceptable salt, hydrate, polymorph, or isomer thereof.

Another embodiment of the invention, encompasses methods of treating inflammation in a subject in need thereof by administering to the subject a formulation having a therapeutically effective amount of a compound 17ya represented:

(17ya)

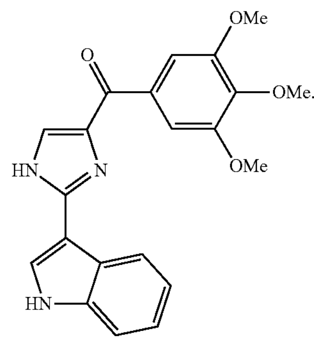

Yet another embodiment of the invention encompasses methods of treating harmful inflammation results from viral infection caused by SARS-CoV, MERS-CoV, COVID-19 or SARS-CoV-2 viruses.

An embodiment of the invention encompasses methods of treating inflammation wherein the compound of the invention is administered in an amount of about 1 mg to about 100 mg. Another embodiment of the invention encompasses methods of treating inflammation wherein the compound of the invention is administered in an amount of about 4 to about 90 mg. Another embodiment of the invention encompasses methods of treating inflammation wherein the compound of the invention is administered in an amount of about 9 mg to about 18 mg. Another embodiment of the invention encompasses methods of treating inflammation wherein the compound of the invention is administered in an amount of about 4 mg to about 45 mg. In yet another embodiment of the methods of treating inflammation encompass at least one pharmaceutically acceptable excipient.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2A illustrates the flow cytometry which counted cells based on TNFα expressing splenocyte cells incubated with lipopolysaccharide (LPS). FIG. 2B illustrates the same flow cytometry of splenocytes incubated with LPS and Compound 17ya (10 nM). FIG. 2C illustrates the flow cytometry of splenocytes incubated with LPS and Compound 17ya (100 nM). FIG. 2D illustrates the flow cytometry of splenocytes incubated with LPS and Compound 17ya (200 nM). FIG. 2E illustrates the flow cytometry of splenocytes incubated with LPS and colchicine (200 nM). FIG. 2F illustrates the flow cytometry of splenocytes of the TNF unstimulated control.

FIG. 3A illustrates the standard curve for the ELISA assay that showed the expected linear response. FIG. 3B illustrates that both Compound 17ya and colchicine significantly suppressed IL-1β secretion in response to nigericin stimulation in a dose dependent manner.

DETAILED DESCRIPTION OF THE INVENTION

Figure 1:
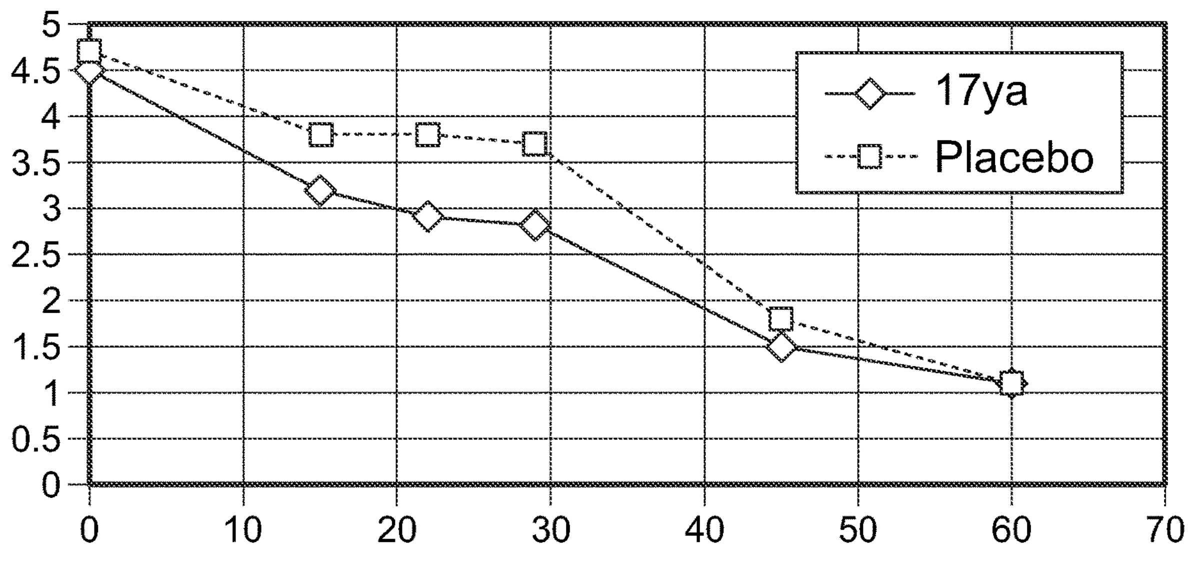
FIG. 1 illustrates the mean WHO Ordinal Scale for Clinical Improvement by Day (0=baseline). The area under the mean curve is 153 for the patient group treated with Compound 17ya and 182 for the group treated with placebo.

Microtubule based macromolecule transport is a critical aspect of viral replication and for triggering the cytokine storm inflammation. For viral infection, expression of viral proteins alters the organization of these microtubular networks to serve their need to replicate and spread infectious virion. Microtubules not only facilitate infection, but microtubules are actively manipulated by viruses. Furthermore, cytoskeleton disruptor agents suppress viral infection.

Not to be limited by theory, the invention is based, in part, on the fact that viruses and the other harmful stimuli (pathogens, damaged cells, toxic compounds, among others) trigger the innate host immune system via activation of NLRP3 inflammasomes. Microtubules are critical for activation of the inflammasomes. Microtubules are required to assemble NLRP3 inflammasomes by transporting the ASC on the mitochondria to the perinuclear region to colocalize together with NLRP3 on the endoplasmic reticulum. Once inflammasome assembly is completed, caspase-1 is activated and processes pro-IL1-β into activated IL1-β and IL-18 which initiates the immune over-reaction leading to the overwhelming release of immune proteins called cytokines and referred to as a cytokine storm. The cytokine storm may lead to acute inflammation that can contribute to a variety of serious human inflammatory diseases such as, but not limited to, gout, arthritis, reaction to viral infections, allergies, asthma, autoimmune diseases, coeliac disease, glomerulonephritis, hepatitis, inflammatory bowel disease, fatty liver disease, type 2 diabetes, atherosclerosis, cancer and many others. For example, key cytokines released during the storm and detected in high levels in the blood from COVID-19 patients include interleukin (IL)-1α, IL-1β, IL-6, IL-8, and Tumor Necrosis Factor α (TNFα).

The present invention is directed to anti-inflammation therapy based upon the cytoskeleton disruptor activity of the claimed compounds that interrupts the intracellular microtubules trafficking network and assembly of inflammasomes. Intended to overcome the disadvantages of the prior art, including but not limited to toxicity, the methods are directed to compounds specifically activated to prevent or reduce the cytokine storm. To address the need for novel, rapidly acting anti-inflammation therapy compounds, the inventors proposed a method of treating inflammation by the administration of the compounds described below.

In a particular embodiment, the compounds of the invention are orally bioavailable non-colchicine molecules that bind the "colchicine binding site" of α and β tubulin and inhibits tubulin polymerization at low nanomolar concentrations. These colchicine binding site inhibitors (CBSIs) have a broad scope of structures but generally possess predominantly indolyl, phenyl, or indazolyl A-rings (leftmost ring in Formula I), direct bond or amino linkers (X) between A- and B-rings, imidazole, or benzimidazole B-rings, methanone linkers (Y) between the B-ring and C-ring (rightmost ring in Formula I), and substituted phenyl C-rings. The compounds used in the methods are neither a substrate for MDRs including P-gp, MRPs, and BCRP, nor CYP3A4. The compounds used in the methods also decrease the transcription of βI, βIII, and βIV-tubulin isoforms (Li 2012). Further, the compounds used in the methods of the invention have good safety as they do not cause significant neurotoxicity, neutropenia, or myelosuppression and are well tolerated.

Further, the methods encompassed by the invention include compounds capable of influencing microtubule dynamics such that the compounds could be administered in sub-cytotoxic concentrations as systemic anti-inflammatory agents. This is in strong contrast to colchicine and other tubulin polymerization destabilizers used as anti-inflammatory drugs which possess high systemic toxicity.

The invention encompasses methods of treating inflammation in a subject in need thereof by administering to the subject a formulation having a therapeutically effective amount of a compound of Formula (I)

(I)

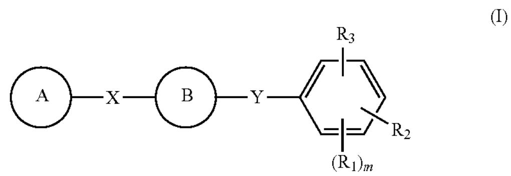

wherein

A is phenyl, indolyl, or indazolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

B is an imidazole, thiazole, or benzimidazole, optionally substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

X is a bond, NH, $(C_1-C_4)$alkyl, O, or S;

Y is a bond, —C═O, —C═S, $SO_2$, SO or S; and m is 1-3, or a pharmaceutically acceptable salt, hydrate, polymorph, or isomer thereof.

The invention also encompasses methods of treating inflammation in a subject in need thereof by administering to the subject a formulation having a therapeutically effective amount of a compound of Formula (II):

II

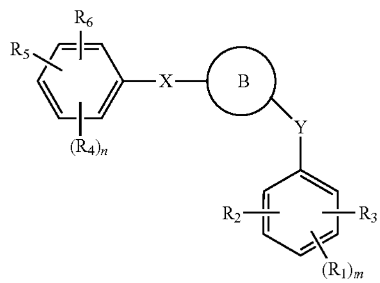

wherein

B is an imidazole, thiazole, or benzimidazole, optionally independently substituted with at least one of $(C_1-C_4)$ alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_1$, $R_2$, $R_3$, $R_4$, $R_5$ and $R_6$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$ alkyl, COOH, —C(O)Ph, C(O)O—$(C_1-C_4)$alkyl, C(O)H, —$C(O)NH_2$ or $NO_2$;

X is a bond or NH;

Y is —C═O;

n is 1-3; and m is 1-3; or a pharmaceutically acceptable salt, hydrate, polymorph, or isomer thereof.

The invention also encompasses methods of treating inflammation in a subject in need thereof by administering to the subject a formulation having a therapeutically effective amount of a compound of Formula (III)

(III)

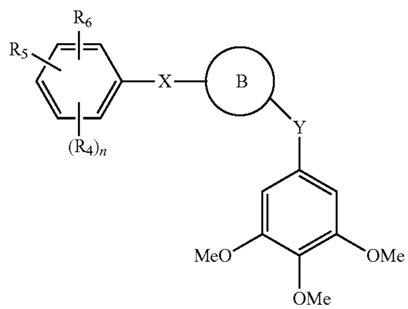

wherein

B is an imidazole, thiazole or benzimidazole, optionally independently substituted with at least one of $(C_1-C_4)$ alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_4$, $R_5$ and $R_6$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

X is a bond or NH;

Y is —C═O; and n is 1-3; or a pharmaceutically acceptable salt, hydrate, polymorph, or isomer thereof.

The invention also encompasses methods of treating inflammation in a subject in need thereof by administering to the subject a formulation having a therapeutically effective amount of a compound of Formula (IV)

(IV)

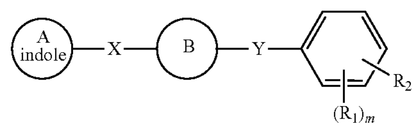

wherein ring A is an indolyl, optionally substituted with at least one of $(C_1-C_4)$alkyl, halo$(C_1-C_4)$alkyl, O—$(C_1-C_4)$ alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

B is an imidazole or benzimidazole, optionally independently substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_1$ and $R_2$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

X is a bond or NH;

Y is —C═O; and m is 1-4; or a pharmaceutically acceptable salt, hydrate, polymorph, or isomer thereof.

The invention also encompasses methods of treating inflammation in a subject in need thereof by administering to the subject a formulation having a therapeutically effective amount of a compound of Formula IV(a)

IV(a)

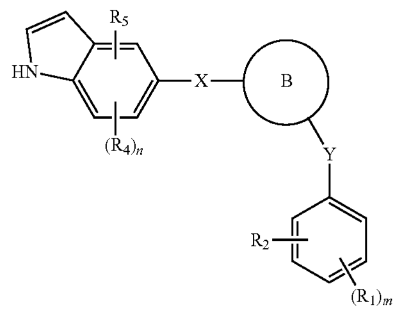

B is an imidazole or benzimidazole, optionally independently substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_1$, $R_2$, $R_4$ and $R_5$ are independently hydrogen, $(C_1-C_4)$ alkyl, halo$(C_1-C_4)$alkyl, O—$(C_1-C_4)$alkyl, O—$(C_1-C_4)$ haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$; and X is a bond or NH;

Y is —C═O;

n is 1-2; and m is 1-4; or a pharmaceutically acceptable salt, hydrate, polymorph, or isomer thereof.

The invention also encompasses methods of treating inflammation in a subject in need thereof by administering to the subject a formulation having a therapeutically effective amount of a compound of Formula (V)

(V)

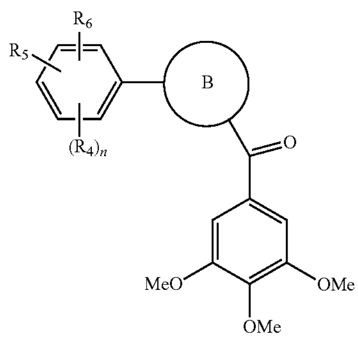

B is an imidazole or benzimidazole, optionally independently substituted with at least one of ($C_1$-$C_4$)alkyl, halo($C_1$-$C_4$)alkyl, O—($C_1$-$C_4$)alkyl, O-halo($C_1$-$C_4$)alkyl, F, Cl, Br, I, CN, —$CH_2$CN, hydroxyl, or $NO_2$;

$R_4$, $R_5$ and $R_6$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

n is 1-3; or a pharmaceutically acceptable salt, hydrate, polymorph, or isomer thereof.

The invention also encompasses methods of treating inflammation in a subject in need thereof by administering to the subject a formulation having a therapeutically effective amount of a compound of the Formula (VI)

(VI)

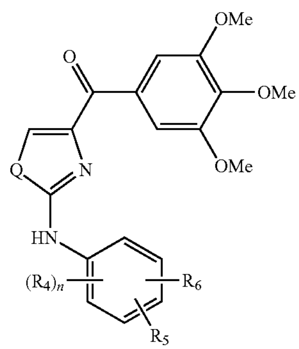

wherein $R_4$, $R_5$ and $R_6$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

Q is NH; and n is 1-3; or a pharmaceutically acceptable salt, hydrate, polymorph, or isomer thereof.

Preferably, the variables for the compounds of Formula (VI) are $R_4$, $R_5$ and $R_6$ are independently hydrogen, ($C_1$-$C_4$)alkyl, halo($C_1$-$C_4$)alkyl, O—(($C_1$-$C_4$)alkyl, O($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; Q is S or NH; and n is 1-3; or a pharmaceutically acceptable salt, hydrate, polymorph, or isomer thereof.

The invention also encompasses methods of treating inflammation in a subject in need thereof by administering to the subject a formulation having a therapeutically effective amount of a compound of the Formula VI in the following Table 1A:

TABLE 1A

| Formula VI | Compound | $R_4$ | $R_5$ | $R_6$ | Q |
|---|---|---|---|---|---|
| 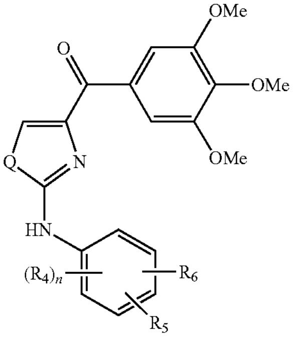 | 5e | H n = 1 | H | H | N |

The invention also encompasses methods of treating inflammation in a subject in need thereof by administering to the subject a formulation having a therapeutically effective amount of a compound of the Formula VII:

(VII)

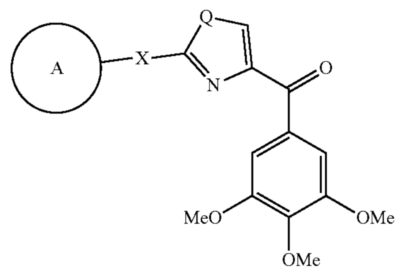

wherein

X is a bond, NH or S;

Q is NH; and

A is a phenyl, indolyl, or indazolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, polymorph, or isomer thereof.

Examples of compounds of Formula VII include, but are not limited to, (2-(phenylamino)-1H-imidazol-4-yl)(3,4,5-trimethoxyphenyl)methanone (Se), (2-(phenylamino)-1H-imidazol-4-yl)(3,4,5-trimethoxyphenyl)methanone hydrochloride salt (5He), and (2-(1H-indol-3-yl)-1H- imidazol-4-yl)(3,4,5-trimethoxyphenyl)methanone (17ya).

Preferably, the variables in the compounds of Formula VII are X is a bond; Q is NH; and A is an indolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, polymorph, or isomer thereof.

The invention also encompasses methods of treating inflammation in a subject in need thereof by administering to the subject a formulation having a therapeutically effective amount of a compound of the Formula VII(a):

VII(a)

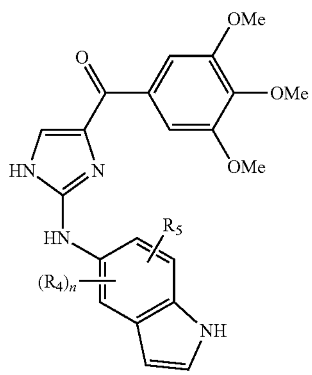

wherein $R_4$ and $R_5$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; and n is 1-4; or a pharmaceutically acceptable salt, hydrate, polymorph, or isomer thereof.

The invention also encompasses methods of treating inflammation in a subject in need thereof by administering to the subject a formulation having a therapeutically effective amount of a compound of the Formula VII(b):

VII(b)

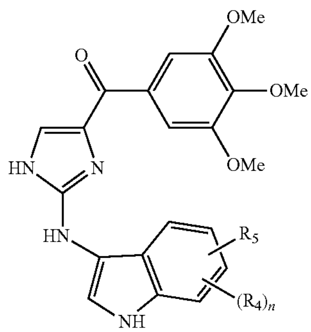

wherein $R_4$ and $R_5$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; and n is 1-4; or a pharmaceutically acceptable salt, hydrate, polymorph, or isomer thereof.

The invention also encompasses methods of treating inflammation in a subject in need thereof by administering to the subject a formulation having a therapeutically effective amount of a compound of the Formula VII(c):

VII(c)

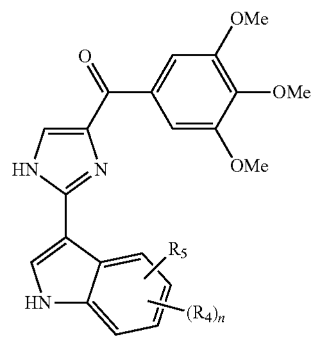

wherein $R_4$ and $R_5$ independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; and n is 1-4; or a pharmaceutically acceptable salt, hydrate, polymorph, or isomer thereof. Examples of compounds of Formula XI(e) include, but are not limited to, (2-(1H-indol-3-yl)-1H-imidazol-4-yl)(3,4,5-trimethoxyphenyl)methanone (17ya).

The invention also encompasses methods of treating inflammation in a subject in need thereof by administering to the subject a formulation having a therapeutically effective amount of a compound of the Formula 17ya:

(17ya)

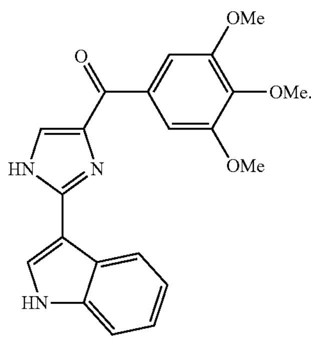

The invention also encompasses methods of treating inflammation in a subject in need thereof by administering to the subject a formulation having a therapeutically effective amount of a compound of the Formula in the following Table 1B:

TABLE 1B
| compound | Structure |
|---|---|
| 8 | 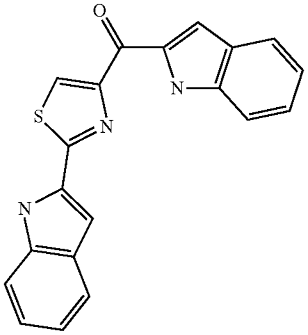 [SMILES: O=C(c1csc(-c2cc3ccccc3[nH]2)n1)c1cc2ccccc2[nH]1] |
| 9 | 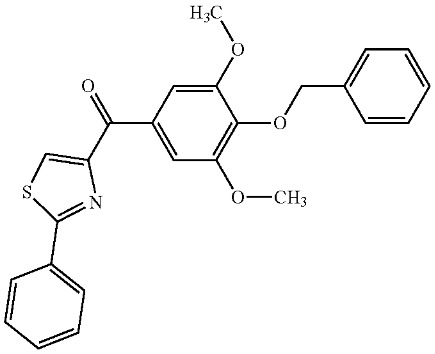 [SMILES: COc1cc(C(=O)c2csc(-c3ccccc3)n2)cc(OC)c1OCc1ccccc1] |
| 10 | 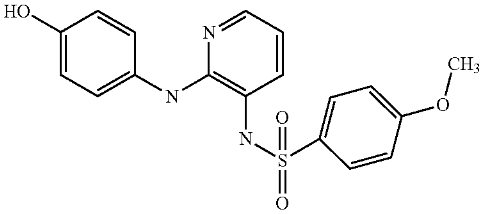 [SMILES: COc1ccc(S(=O)(=O)Nc2cccnc2Nc2ccc(O)cc2)cc1] |
| 11 | 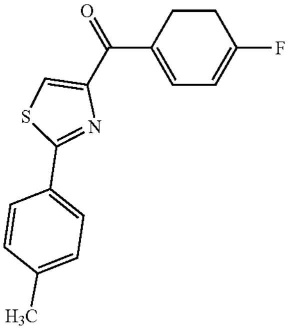 [SMILES: Cc1ccc(-c2nc(C(=O)C3=CC=C(F)CC3)cs2)cc1] |
| 12 | 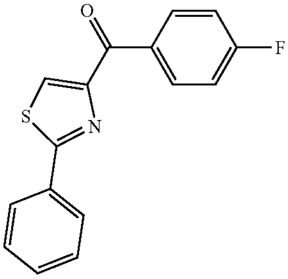 [SMILES: O=C(c1ccc(F)cc1)c1csc(-c2ccccc2)n1] |
TABLE 1B-continued
| compound | Structure |
|---|---|
| 13 | 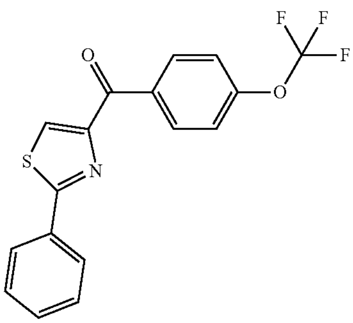 [SMILES: O=C(c1ccc(OC(F)(F)F)cc1)c1csc(-c2ccccc2)n1] |
| 14 | 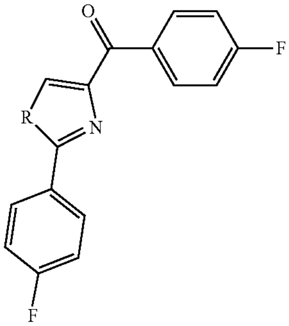 |
| 16 | 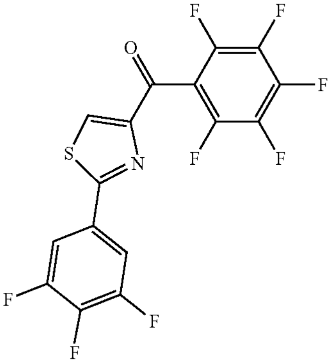 [SMILES: O=C(c1csc(-c2cc(F)c(F)c(F)c2)n1)c1c(F)c(F)c(F)c(F)c1F] |
| 17 | 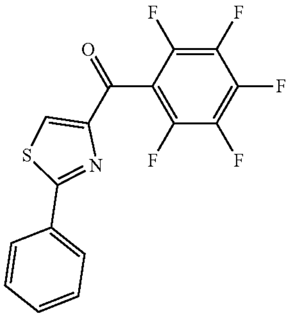 [SMILES: O=C(c1csc(-c2ccccc2)n1)c1c(F)c(F)c(F)c(F)c1F] |

TABLE 1B-continued
| compound | Structure |
| --- | --- |
| 18 | 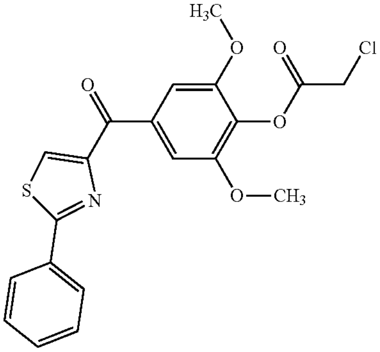 [SMILES: COc1cc(C(=O)c2csc(-c3ccccc3)n2)cc(OC)c1OC(=O)CCl] |
| 19 | 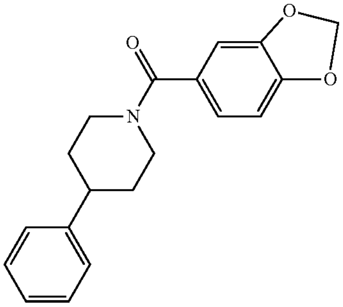 [SMILES: O=C(c1ccc2c(c1)OCO2)N1CCC(c2ccccc2)CC1] |
| 20 | 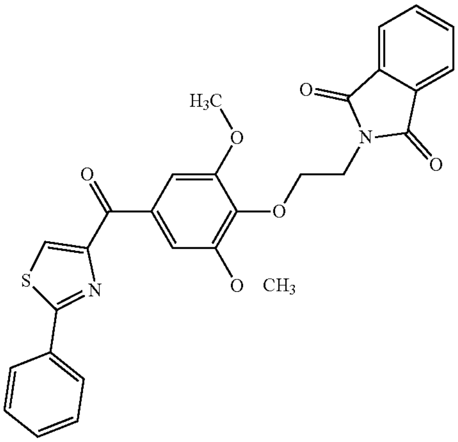 |
| 21 | 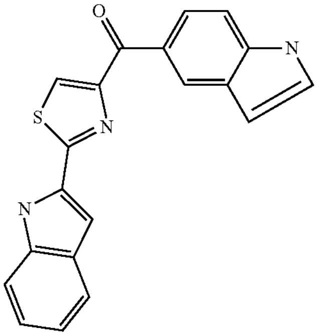 [SMILES: O=C(c1ccc2[nH]ccc2c1)c1csc(-c2cc3ccccc3[nH]2)n1] |
TABLE 1B-continued
| compound | Structure |
| --- | --- |
| 22 | 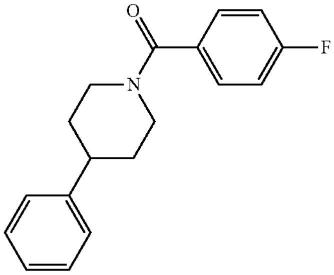 [SMILES: O=C(c1ccc(F)cc1)N1CCC(c2ccccc2)CC1] |
| 23 | 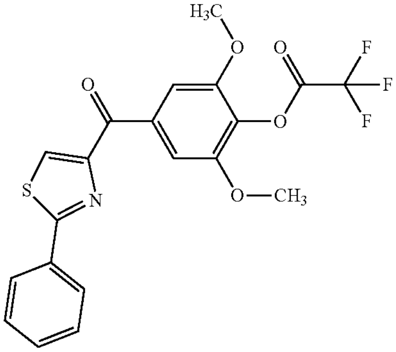 [SMILES: COc1cc(C(=O)c2csc(-c3ccccc3)n2)cc(OC)c1OC(=O)C(F)(F)F] |
| 24 | 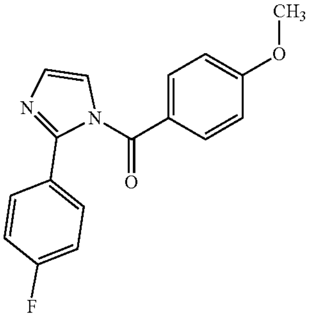 [SMILES: COc1ccc(C(=O)n2ccnc2-c2ccc(F)cc2)cc1] |
| 25 | 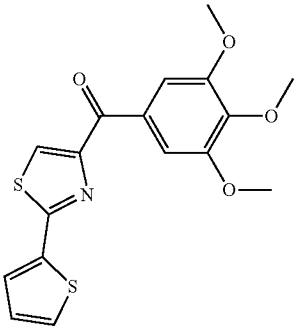 [SMILES: COc1cc(C(=O)c2csc(-c3cccs3)n2)cc(OC)c1OC] |
| 26 | 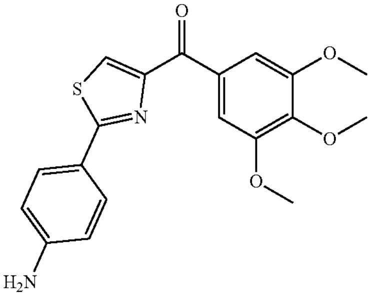 [SMILES: COc1cc(C(=O)c2csc(-c3ccc(N)cc3)n2)cc(OC)c1OC] |

TABLE 1B-continued
| compound | Structure |
| --- | --- |
| 27 | 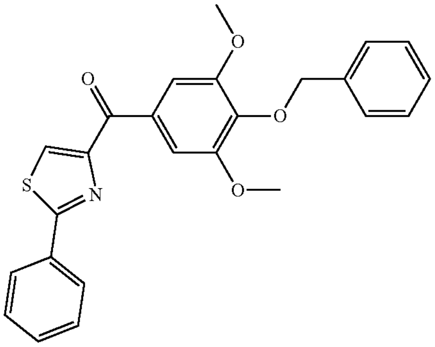 [SMILES: COc1cc(C(=O)c2csc(-c3ccccc3)n2)cc(OC)c1OCc1ccccc1] |
| 28 | 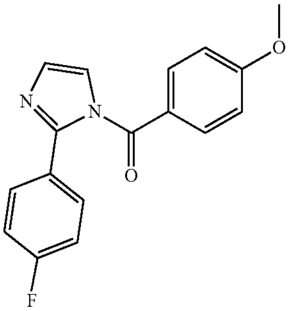 [SMILES: COc1ccc(C(=O)n2ccnc2-c2ccc(F)cc2)cc1] |
| 29 | 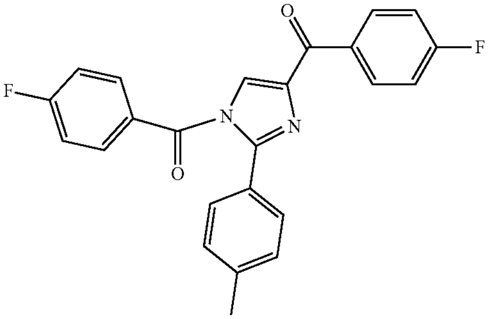 [SMILES: Cc1ccc(-c2nc(C(=O)c3ccc(F)cc3)cn2C(=O)c2ccc(F)cc2)cc1] |
| 30 | 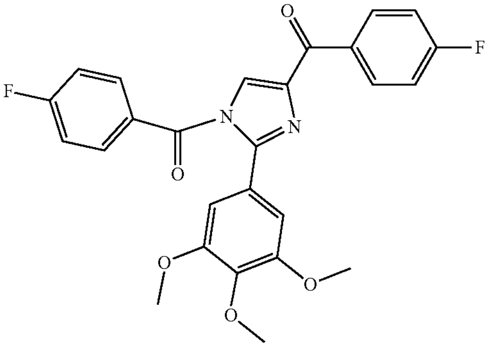 [SMILES: COc1cc(-c2nc(C(=O)c3ccc(F)cc3)cn2C(=O)c2ccc(F)cc2)cc(OC)c1OC] |
TABLE 1B-continued
| compound | Structure |
| --- | --- |
| 32 | 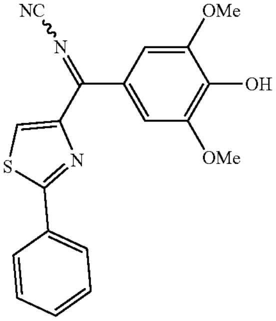 [SMILES: COc1cc(C(=NC#N)c2csc(-c3ccccc3)n2)cc(OC)c1O] |
| 33 | 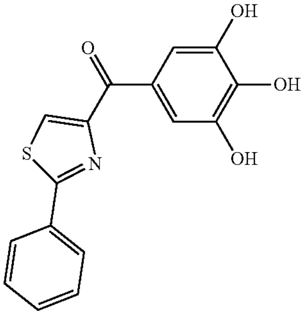 [SMILES: O=C(c1cc(O)c(O)c(O)c1)c1csc(-c2ccccc2)n1] |
| 34 | 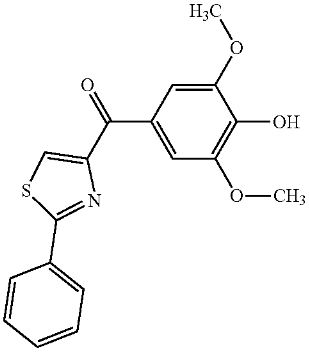 [SMILES: COc1cc(C(=O)c2csc(-c3ccccc3)n2)cc(OC)c1O] |
| 35 | 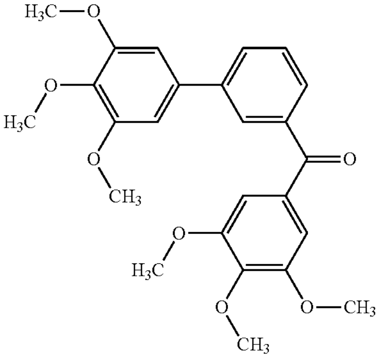 |

TABLE 1B-continued
| compound | Structure |
| --- | --- |
| 40 | 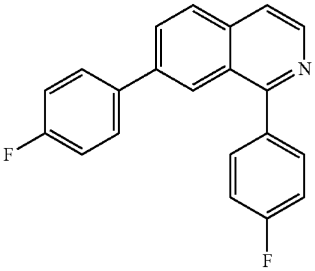 [SMILES: Fc1ccc(-c2ccc3ccnc(-c4ccc(F)cc4)c3c2)cc1] |
| 41 | 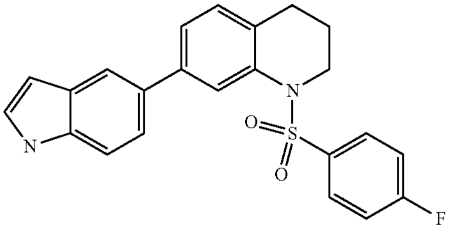 [SMILES: O=S(=O)(c1ccc(F)cc1)N1CCCc2ccc(-c3ccc4[nH]ccc4c3)cc21] |
| 42 | 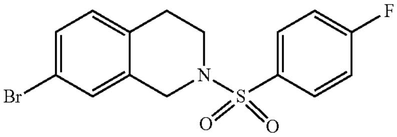 [SMILES: O=S(=O)(c1ccc(F)cc1)N1CCc2ccc(Br)cc2C1] |
| 43 | 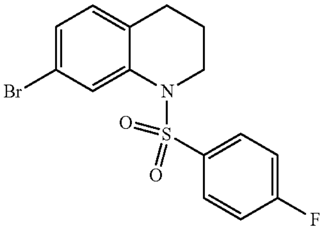 [SMILES: O=S(=O)(c1ccc(F)cc1)N1CCCc2ccc(Br)cc21] |
| 44 | 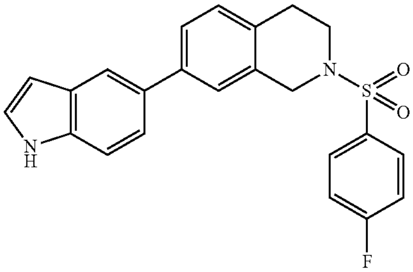 [SMILES: O=S(=O)(c1ccc(F)cc1)N1CCc2ccc(-c3ccc4[nH]ccc4c3)cc2C1] |
| 45 | 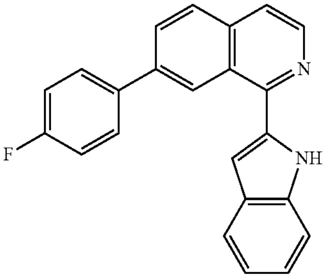 [SMILES: Fc1ccc(-c2ccc3ccnc(-c4cc5ccccc5[nH]4)c3c2)cc1] |
| 46 | 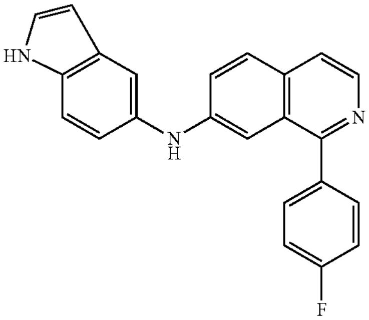 [SMILES: Fc1ccc(-c2nccc3ccc(Nc4ccc5[nH]ccc5c4)cc23)cc1] |
| 47 | 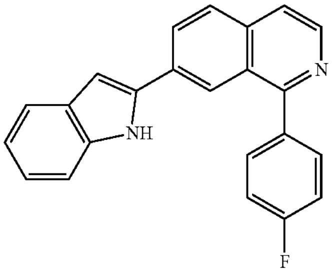 [SMILES: Fc1ccc(-c2nccc3ccc(-c4cc5ccccc5[nH]4)cc23)cc1] |
| 48 | 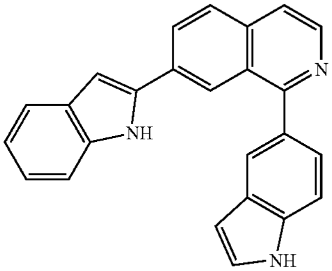 [SMILES: c1ccc2[nH]c(-c3ccc4ccnc(-c5ccc6[nH]ccc6c5)c4c3)cc2c1] |
| 49 | 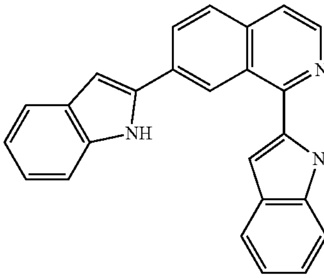 |
| 50 | 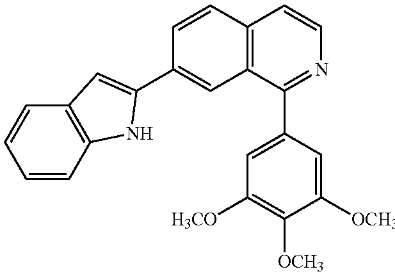 [SMILES: COc1cc(-c2nccc3ccc(-c4cc5ccccc5[nH]4)cc23)cc(OC)c1OC] |

TABLE 1B-continued

| compound | Structure |
| --- | --- |
| 51 | 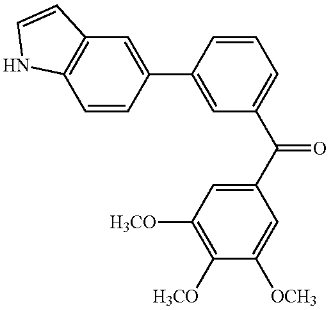 [SMILES: COc1cc(C(=O)c2cccc(-c3ccc4[nH]ccc4c3)c2)cc(OC)c1OC] |
| 52 | 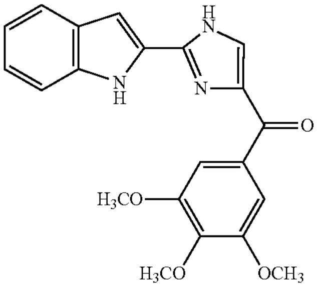 [SMILES: COc1cc(C(=O)c2c[nH]c(-c3cc4ccccc4[nH]3)n2)cc(OC)c1OC] |
| 53 | 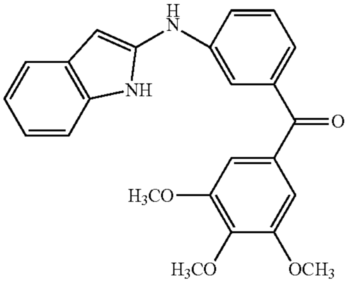 [SMILES: COc1cc(C(=O)c2cccc(Nc3cc4ccccc4[nH]3)c2)cc(OC)c1OC] |
| 54 | 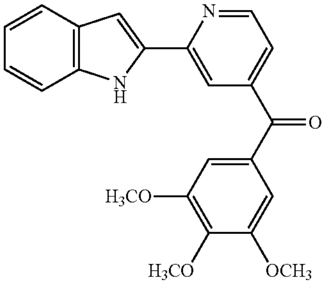 [SMILES: COc1cc(C(=O)c2ccnc(-c3cc4ccccc4[nH]3)c2)cc(OC)c1OC] |

The invention also encompasses methods of treating inflammation in a subject in need thereof by administering to the subject a formulation having a therapeutically effective amount of a compound of the Formula XIII:

(XIII)

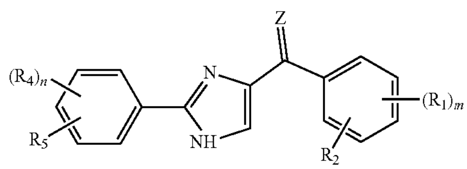

wherein

Z is O;

$R_1$ and $R_4$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

$R_2$ and $R_5$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

m is an integer between 1-4; and n is an integer between 1-4;

or a pharmaceutically acceptable salt, hydrate, polymorph, or isomer.

The invention also encompasses methods of treating inflammation in a subject in need thereof by administering to the subject a formulation having a therapeutically effective amount of a compound of the Formula XIV:

(XIV)

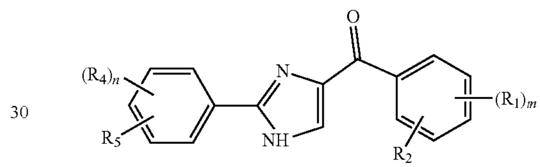

wherein $R_1$ and $R_4$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

$R_2$ and $R_5$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO-alkyl, COOH, —C(O)Ph, C(O)O—$(C_1$-$C_4)$alkyl, C(O)H, —$C(O)NH_2$ or $NO_2$;

m is an integer between 1-4; and n is an integer between 1-4;

or a pharmaceutically acceptable salt, hydrate, polymorph, or isomer thereof.

Non limiting examples of compounds of formula XIV are selected from: (2-phenyl-1H-imidazol-4-yl)(3,4,5-trimethoxyphenyl)methanone (12aa), (4-fluorophenyl)(2-phenyl-1H-imidazol-4-yl)methanone (12af), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl)methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-hydroxy-3,5-dimethoxyphenyl)(2-(p-tolyl)-1H-imidazol-4-yl)methanone (12dc), (2-(4-chlorophenyl)-1H-imidazol-4-yl)(3,4,5-trimethoxyphenyl)methanone (12fa), (2-(4-chlorophenyl)-1H-imidazol-4-yl)(4-fluorophenyl)methanone (12fb), (2-(4-chlorophenyl)-1H-imidazol-4-yl)(4-hydroxy-3,5-dimethoxyphenyl)methanone (12fc), (2-(4-(dimethylamino)phenyl)-1H-imidazol-4-yl)(3,4,5- trimethoxyphenyl)methanone (12ga), (2-(4-(dimethylamino)phenyl)-1H-imidazol-4-yl)(4-fluorophenyl)methanone (12gb), (2-(3,4-dimethoxyphenyl)-1H-imidazol-4-yl)(3,4,5-trimethoxyphenyl)methanone (12ha), (2-(4-(benzyloxy)phenyl)-1H-imidazol-4-yl)(4-fluorophenyl)methanone (12jb), (2-(4-bromophenyl)-1H-imidazol-4-yl)(3,4,5-trimethoxyphenyl)methanone (12la), (2-(4-(trifluoromethyl)phenyl)-1H-imidazol-4-yl)(3,4,5-trimethoxyphenyl)methanone (12pa).

The invention also encompasses methods of treating inflammation in a subject in need thereof by administering to the subject a formulation having a therapeutically effective amount of a compound of the Formula XIVa:

(XIVa)

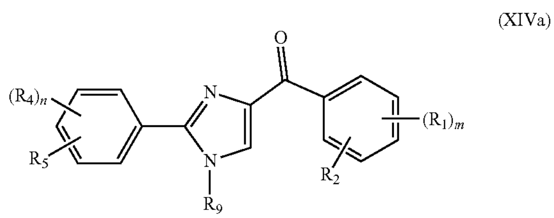

wherein $R_1$ and $R_4$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

$R_2$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

$R_9$ is H, linear or branched, alkyl, aryl, $CH_2Ph$, benzyl, haloalkyl, aminoalkyl, $OCH_2Ph$, $SO_2$-Aryl, —(C═O)-Aryl or OH, optionally substituted with at least one of hydrogen, hydroxyl, an aliphatic straight- or branched-chain $C_1$ to $C_{10}$ hydrocarbon, alkoxy, haloalkoxy, aryloxy, nitro, cyano, alkyl-CN, halo (e.g., F, Cl, Br, I), haloalkyl, dihaloalkyl, trihaloalkyl, COOH, C(O)Ph, C(O)-alkyl, C(O)O-alkyl, C(O)H, $C(O)NH_2$, —$OC(O)CF_3$, $OCH_2Ph$, amino, aminoalkyl, alkylamino, mesylamino, dialkylamino, arylamino, amido, NHC(O)-alkyl, urea, alkyl-urea, alkylamido (e.g., acetamide), haloalkylamido, arylamido, aryl, and $C_5$ to $C_7$ cycloalkyl, arylalkyl, and combinations thereof;

m is an integer between 1-4; and n is an integer between 1-4;

or a pharmaceutically acceptable salt, hydrate, polymorph, or isomer thereof.

Non limiting examples of compounds of formula XIVa are selected from: (4-fluorophenyl)(2-phenyl-1-(phenylsulfonyl)-1H-imidazol-4-yl)methanone (11af), (4-fluorophenyl)(2-(4-methoxyphenyl)-1-(phenylsulfonyl)-1H-imidazol-4-yl)methanone (11cb), (4-fluorophenyl)(1-(phenylsulfonyl)-2-(p-tolyl)-1H-imidazol-4-yl)methanone (11db), (2-(4-chlorophenyl)-1-(phenylsulfonyl)-1H-imidazol-4-yl)(4-fluorophenyl)methanone (11fb), (2-(4-(dimethylamino)phenyl)-1-(phenylsulfonyl)-1H-imidazol-4-yl)(3,4,5-trimethoxyphenyl)methanone (11ga), (2-(4-

(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11ha), (2-(4-(benzyloxy)phenyl)-1-(phenylsulfonyl)-1H-imidazol-4-yl)(4-fluorophenyl)methanone (11jb), (2-(4-(dimethylamino)phenyl)-1-((4-methoxyphenyl)sulfonyl)-1H-imidazol-4-yl)(4-fluorophenyl)methanone (12gba), (1-benzyl-2-(p-tolyl)-1H-imidazol-4-yl)(3,4,5-trimethoxyphenyl)methanone (12daa), (1-methyl-2-(p-tolyl)-1H-imidazol-4-yl)(3,4,5-trimethoxyphenyl)methanone (12dab), (4-fluorophenyl)(2-(4-methoxyphenyl)-1-methyl-1H-imidazol-4-yl)methanone (12cba).

The invention also encompasses methods of treating inflammation in a subject in need thereof by administering to the subject a formulation having a therapeutically effective amount of a compound of the Formula XV:

(XV)

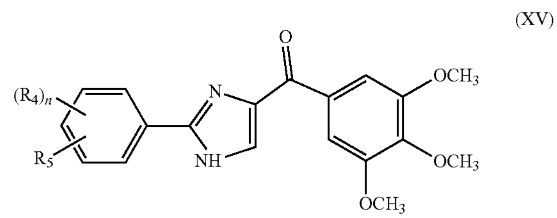

wherein $R_4$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; and n is 1-4; or a pharmaceutically acceptable salt, hydrate, polymorph, or isomer thereof.

Non limiting examples of compounds of formula XV are selected from: (2-phenyl-1H-imidazol-4-yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (3,4,5-trimethoxyphenyl)(2-(3,4,5-trimethoxyphenyl)-1H-imidazol-4-yl)methanone (12ea.), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(3,4-dimethoxyphenyl)-1H-imidazol-4-yl)(3,4,5-trimethoxyphenyl)methanone (12ha), (2-(2-(trifluoromethyl)phenyl)-1H-imidazol-4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (12la), and (2-(4-(trifluoromethyl)phenyl)-1H-imidazol-4-yl)(3,4,5-trimethoxyphenyl)methanone (12pa).

The invention also encompasses methods of treating inflammation in a subject in need thereof by administering to the subject a formulation having a therapeutically effective amount of a compound of the Formula XVI:

(XVI)

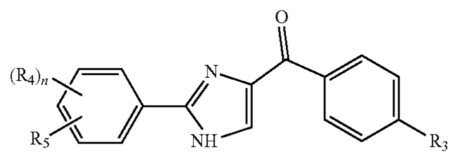

wherein $R_4$ and $R_5$ are independently hydrogen, $(C_1-C_4)$ alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

$R_3$ is I, Br, Cl, or F; and n is 1-4; or a pharmaceutically acceptable salt, hydrate, polymorph, or isomer.

Non limiting examples of compounds of formula XVI are selected from: (4-fluorophenyl)(2-phenyl-1H-imidazol-4-yl)methanone (12af), (4-fluorophenyl)(2-(4-methoxyphenyl)-1H-imidazol-4-yl)methanone (12cb), (4-fluorophenyl)(2-(p-tolyl)-1H-imidazol-4-yl)methanone (12db), 4-fluorophenyl)(2-(3,4,5-trimethoxyphenyl)-1H-imidazol-4-yl)methanone (12eb), (2-(4-chlorophenyl)-1H-imidazol-4-yl)(4-fluorophenyl)methanone (12fb), (2-(4-(dimethylamino)phenyl)-1H-imidazol-4-yl)(4-fluorophenyl) methanone (12gb), (2-(4-(benzyloxy)phenyl)-1H-imidazol-4-yl)(4-fluorophenyl)methanone (12jb).

The invention also encompasses methods of treating inflammation in a subject in need thereof by administering to the subject a formulation having a therapeutically effective amount of a compound of the Formula XVII:

(XVII)

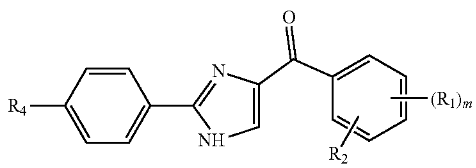

wherein $R_4$ is H, O—$(C_1-C_4)$alkyl, I, Br, Cl, F, $(C_1-C_4)$alkyl, halo$(C_1-C_4)$alkyl, amino$(C_1-C_4)$alkyl, $OCH_2Ph$, OH, CN, $NO_2$, —NHCO—$(C_1-C_4)$alkyl, COOH, C(O)O—$(C_1-C_4)$ alkyl or C(O)H;

wherein $R_1$ and $R_2$ are independently H, O-alkyl, I, Br, Cl, F, $(C_1-C_4)$alkyl, halo$(C_1-C_4)$alkyl, amino$(C_1-C_4)$alkyl, $OCH_2Ph$, OH, CN, $NO_2$, —NHCO—$(C_1-C_4)$alkyl, COOH, C(O)O—$(C_1-C_4)$alkyl or C(O)H; and m is 1-4; or a pharmaceutically acceptable salt, hydrate, polymorph, or isomer thereof.

Non limiting examples of compounds of formula XVII are selected from: (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl)methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-hydroxy-3,5-dimethoxyphenyl)(2-(p-tolyl)-1H-imidazol-4-yl)methanone (12dc), (2-(4-chlorophenyl)-1H-imidazol-4-yl)(3,4,5-trimethoxyphenyl)methanone (12fa), (2-(4-chlorophenyl)-1H-imidazol-4-yl)(4-fluorophenyl) methanone (12fb), (2-(4-chlorophenyl)-1H-imidazol-4-yl) (3,4,5-trihydroxyphenyl)methanone (13fa), (2-(4-(dimethylamino)phenyl)-1H-imidazol-4-yl)(3,4,5-trimethoxyphenyl) methanone (12ga), (2-(4-(dimethylamino)phenyl)-1H-imidazol-4-yl)(4-fluorophenyl)methanone (12gb), (2-(4-(benzyloxy)phenyl)-1H-imidazol-4-yl)(4-fluorophenyl) methanone (12jb), (2-(4-hydroxyphenyl)-1H-imidazol-4-yl) (3,4,5-trimethoxyphenyl)methanone (12ka), (2-(4-bromophenyl)-1H-imidazol-4-yl)(3,4,5-trimethoxyphenyl) methanone (12la), and (2-(4-(trifluoromethyl)phenyl)-1H-imidazol-4-yl)(3,4,5-trimethoxyphenyl)methanone (12pa).

The invention also encompasses methods of treating inflammation in a subject in need thereof by administering to the subject a formulation having a therapeutically effective amount of a compound of the Formula XVII represented by the structure of formula 12fb:

(12fb)

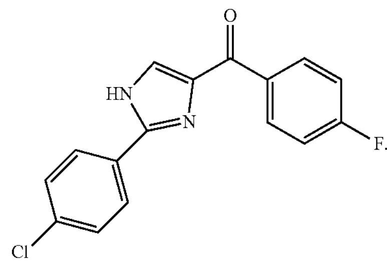

The invention also encompasses methods of treating inflammation in a subject in need thereof by administering to the subject a formulation having a therapeutically effective amount of a compound of the Formula XVII represented by the structure of formula 12cb:

(12cb)

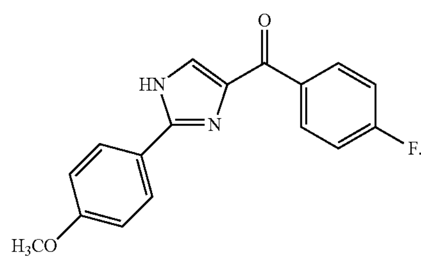

Non limiting examples of compounds are selected from: (4-methoxyphenyl)(2-phenyl-1H-imidazol-1-yl)methanone (12aba), (2-phenyl-1H-imidazol-1-yl)(3,4,5-trimethoxyphenyl)methanone (12aaa), 2-phenyl-1-(phenylsulfonyl)-1H-imidazole (10a), 2-(4-nitrophenyl)-1-(phenylsulfonyl)-1H-imidazole (10x), 2-(4-(benzyloxy)phenyl)-1-(phenylsulfonyl)-1H-imidazole (10j).

The invention also encompasses methods of treating inflammation in a subject in need thereof by administering to the subject a formulation having a therapeutically effective amount of a compound of the Formula XIX:

(XIX)

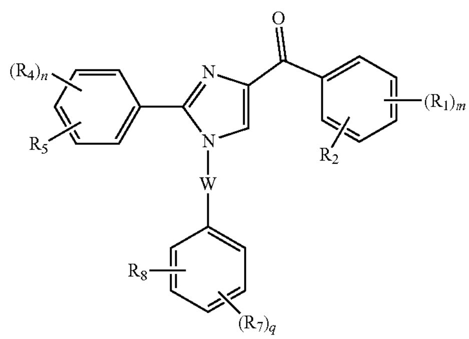

wherein

W is C═O, C═S, $SO_2$, S═O;

$R_1$, $R_4$ and $R_7$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

$R_2$, $R_5$ and $R_8$ are independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl COOH, —C(O)Ph, C(O)O—$(C_1-C_4)$alkyl, C(O)H, —$C(O)NH_2$ or $NO_2$;

m is 1-4;

n is 1-4; and q is 1-4;

or its pharmaceutically acceptable salt, hydrate, polymorph, or isomer.

Non limiting examples of compounds of formula XIX are selected from: (2-(4-(dimethylamino)phenyl)-1-((4-methoxyphenyl)sulfonyl)-1H-imidazol-4-yl)(3,4,5-trimethoxyphenyl)methanone (11gaa); (2-(4-bromophenyl)-1-(phenylsulfonyl)-1H-imidazol-4-yl)(3,4,5-trimethoxyphenyl)methanone (11la), (4-fluorophenyl)(2-(4-methoxyphenyl)-1-(phenylsulfonyl)-1H-imidazol-4-yl)methanone (11cb), (2-(4-chlorophenyl)-1-(phenylsulfonyl)-1H-imidazol-4-yl)(4-fluorophenyl)methanone (11fb), (4-fluorophenyl)(2-phenyl-1-(phenylsulfonyl)-1H-imidazol-4-yl)methanone (11af), (4-fluorophenyl)(1-(phenylsulfonyl)-2-(p-tolyl)-1H-imidazol-4-yl)methanone (11db), (2-(4-(dimethylamino)phenyl)-1-(phenylsulfonyl)-1H-imidazol-4-yl)(3,4,5-trimethoxyphenyl)methanone (11ga), (2-(4-(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11ha), (2-(4-(benzyloxy)phenyl)-1-(phenylsulfonyl)-1H-imidazol-4-yl)(4-fluorophenyl)methanone (11jb), (2-(4-(dimethylamino)phenyl)-1-((4-methoxyphenyl)sulfonyl)-1H-imidazol-4-yl)(4-fluorophenyl)methanone (12gba).

The invention also encompasses methods of treating inflammation in a subject in need thereof by administering to the subject a formulation having a therapeutically effective amount of a compound of the Formula XIX represented by the structure of formula 11cb:

(11cb)

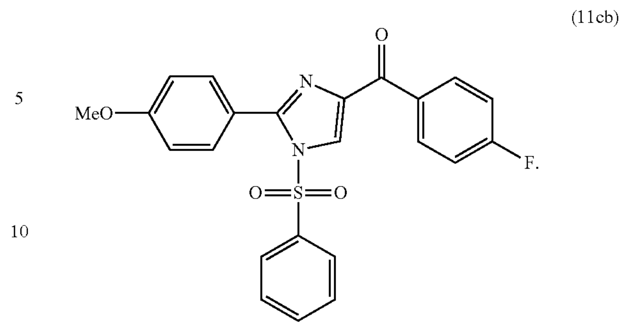

The invention also encompasses methods of treating inflammation in a subject in need thereof by administering to the subject a formulation having a therapeutically effective amount of a compound of the Formula XIX represented by the structure of formula 11fb:

(11fb)

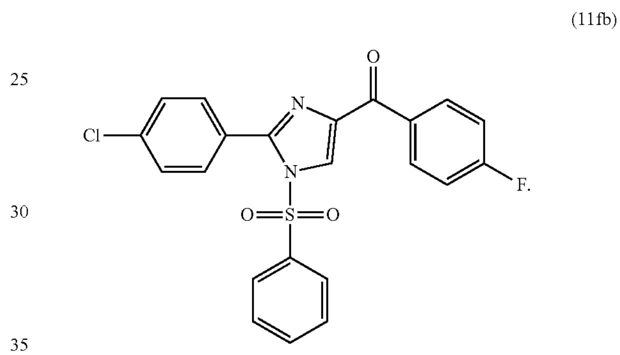

The invention also encompasses methods of treating inflammation in a subject in need thereof by administering to the subject a formulation having a therapeutically effective amount of a compound of the Formula XX:

(XX)

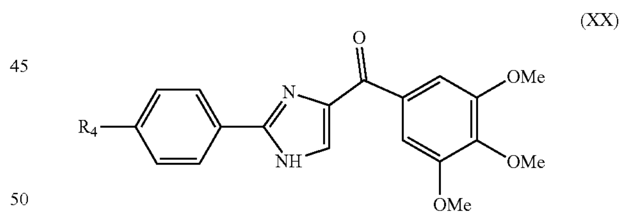

wherein $R_4$ is independently hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$; or a pharmaceutically acceptable salt, hydrate, polymorph, or isomer.

Non limiting examples of compounds of formula XX are selected from: (2-phenyl-1H-imidazol-4-yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(2-(trifluoromethyl)phenyl)-1H-imidazol-4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (12la), (2-(4-(trifluoromethyl)phenyl)-1H-imidazol-4-yl)(3,4,5-trimethoxyphenyl)methanone (12pa).

The invention also encompasses methods of treating inflammation in a subject in need thereof by administering to the subject a formulation having a therapeutically effective amount of a compound of the Formula XX represented by the structure of formula 12da:

(12da)

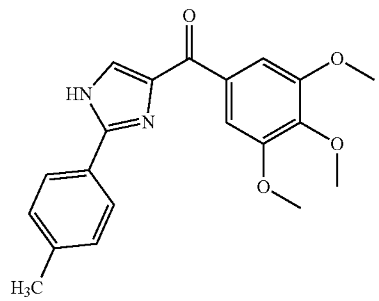

The invention also encompasses methods of treating inflammation in a subject in need thereof by administering to the subject a formulation having a therapeutically effective amount of a compound of the Formula XX represented by the structure of formula 12fa:

(12fa)

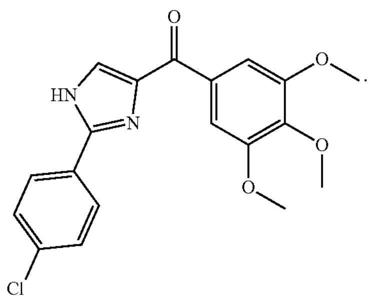

The invention also encompasses methods of treating inflammation in a subject in need thereof by administering to the subject a formulation having a therapeutically effective amount of a compound of the Formula XXI:

(XXI)

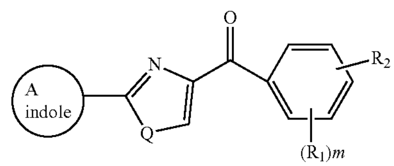

wherein

A is indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

Q is NH;

$R_1$ and $R_2$ are independently hydrogen, $(C_1-C_4)$alkyl, halo(O—$C_4$)alkyl, O—$(C_1-C_4)$alkyl, O—$(C_1-C_4)$haloalkyl, $C_4$)alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$; and m is 1-4; or a pharmaceutically acceptable salt, hydrate, polymorph, or isomer thereof.

In one embodiment of the method of treating inflammation, A ring of compound of formula XXI is substituted 5-indolyl. In another embodiment the substitution is —(C═O)-Aryl. In another embodiment, the aryl is 3,4,5-$(OCH_3)_3$-Ph. In another embodiment, A ring of compound of formula XXI is 3-indolyl. In another embodiment, A ring of compound of formula XXI is 5-indolyl. In another embodiment, A ring of compound of formula XXI is 2-indolyl. Non limiting examples of compounds of formula XXI are selected from: (5-(4-(3,4,5-trimethoxybenzoyl)-1H-imidazol-2-yl)-1H-indol-2-yl)(3,4,5-trimethoxyphenyl)methanone (15xaa); (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); (2-(1H-indol-3-yl)-1H-imidazol-4-yl)(3,4,5-trimethoxyphenyl)methanone (17ya); (2-(1H-indol-2-yl)thiazol-4-yl)(3,4,5-trimethoxyphenyl)methanone (62a); and (2-(1H-indol-5-yl)thiazol-4-yl)(3,4,5-trimethoxyphenyl)methanone (66a).

A particularly preferred method of treating inflammation of the invention uses at least one compound of formula XXI including 2-(1H-indol-1-yl)-1H-imidazol-4-yl)(3,4,5-trimethoxyphenyl)methanone; 2-(1H-indol-2-yl)-1H-imidazol-4-yl)(3,4,5-trimethoxyphenyl)methanone; (2-(1H-indol-3-yl)-1H-imidazol-4-yl)(3,4,5-trimethoxyphenyl)methanone (17ya); 2-(1H-indol-4-yl)-1H-imidazol-4-yl)(3,4,5-trimethoxyphenyl)methanone; 2-(1H-indol-5-yl)-1H-imidazol-4-yl)(3,4,5-trimethoxyphenyl)methanone; 2-(1H-indol-6-yl)-1H-imidazol-4-yl)(3,4,5-trimethoxyphenyl)methanone; or 2-(1H-indol-7-yl)-1H-imidazol-4-yl)(3,4,5-trimethoxyphenyl)methanone.

The invention also encompasses methods of treating inflammation in a subject in need thereof by administering to the subject a formulation having a therapeutically effective amount of a compound of the Formula XXIa:

(XXIa)

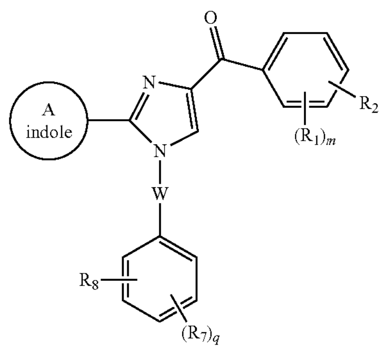

wherein

W is C═O, C═S, $SO_2$, or S═O;

A is indolyl optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

$R_1$ and $R_2$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

$R_7$ and $R_8$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

m is 1-4; and q is 1-4; or a pharmaceutically acceptable salt, hydrate, polymorph, or isomer thereof.

Non limiting examples of compounds of formula XXIa are selected from: (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); (1-(phenylsulfonyl)-2-(1-(phenylsulfonyl)-1H-indol-3-yl)-1H-imidazol-4-yl)(3,4,5-trimethoxyphenyl)methanone (17yaa).

The invention also encompasses methods of treating inflammation in a subject in need thereof by administering to the subject a formulation having a therapeutically effective amount of a compound of the Formula XXII:

(XXII)

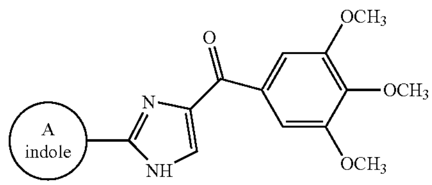

wherein

A is indolyl optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

or a pharmaceutically acceptable salt, hydrate, polymorph, or isomer thereof.

In one embodiment of the method of treating inflammation, A ring of compound of formula XXII is substituted 5-indolyl. In another embodiment the substitution is —(C═O)-Aryl. In another embodiment, the aryl is 3,4,5-$(OCH_3)_3$-Ph. In another embodiment, A ring of compound of formula XXII is 3-indolyl. Non limiting examples of compounds of formula XXII are selected from: (5-(4-(3,4,5-trimethoxybenzoyl)-1H-imidazol-2-yl)-1H-indol-2-yl)(3,4,5-trimethoxyphenyl)methanone (15xaa); and (2-(1H-indol-3-yl)-1H-imidazol-4-yl)(3,4,5-trimethoxyphenyl)methanone (17ya).

The invention also encompasses methods of treating inflammation in a subject in need thereof by administering to the subject a formulation having a therapeutically effective amount of a compound of the Formula XXI or XXII represented by the structure of formula 17ya:

(17ya)

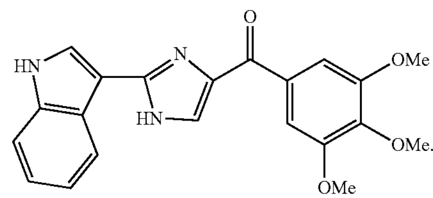

In one embodiment of the method, $R_4$ and $R_5$ of compounds of formula XIII-XVI are hydrogens. Non-limiting examples of compounds of formula XIII-XVI wherein $R_4$ and $R_5$ are hydrogens are selected from (2-phenyl-1H-imidazol-4-yl)(3,4,5-trimethoxyphenyl)methanone (12aa); (4-methoxyphenyl)(2-phenyl-1H-imidazol-4-yl)methanone (12ab); (3-methoxyphenyl)(2-phenyl-1H-imidazol-4-yl)methanone (12ac); (3,5-dimethoxyphenyl)(2-phenyl-1H-imidazol-4-yl)methanone (12ad); (3,4-dimethoxyphenyl)(2-phenyl-1H-imidazol-4-yl)methanone (12ae); (4-fluorophenyl)(2-phenyl-1H-imidazol-4-yl)methanone (12af); (3-fluorophenyl)(2-phenyl-1H-imidazol-4-yl)methanone (12ag); (2-phenyl-1H-imidazol-4-yl)(p-tolyl)methanone (12ah); and (2-phenyl-1H-imidazol-4-yl)(m-tolyl)methanone (12ai).

In one embodiment of the method, the compounds of this invention are the pure (E)-isomers. In another embodiment, the compounds of this invention are the pure (Z)-isomers. In another embodiment, the compounds of this invention are a mixture of the (E) and the (Z) isomers. In one embodiment, the compounds of this invention are the pure (R)-isomers. In another embodiment, the compounds of this invention are the pure (S)-isomers. In another embodiment, the compounds of this invention are a mixture of the (R) and the (S) isomers.

The compounds of the present invention can also be present in the form of a racemic mixture, containing substantially equivalent amounts of stereoisomers. In another embodiment, the compounds of the present invention can be prepared or otherwise isolated, using known procedures, to obtain a stereoisomer substantially free of its corresponding stereoisomer (i.e., substantially pure). As used herein, the term "substantially pure" refers to stereoisomer is at least about 95% pure in one isomer. Alternatively, the stereoisomer purity may be at least about 98% pure, and more preferably at least about 99% pure.

Compounds can also be in the form of a hydrate, which means that the compound further includes a stoichiometric or non-stoichiometric amount of water bound by non-covalent intermolecular forces.

The invention includes "pharmaceutically acceptable salts" of the compounds used in the method of the invention, which may be produced, by reaction of a compound of this invention with an acid or base. Certain compounds, particularly those possessing acid or basic groups, can also be in the form of a salt, preferably a pharmaceutically acceptable salt. As used herein, the term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of compounds used in the method of the invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

Examples of organic salts of amines include, but are not limited to, aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

Examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

Examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

Typical salts include, but are not limited to, hydrofluoric, hydrochloric, hydrobromic, hydroiodic, boric, nitric, perchloric, phosphoric, sulfuric, acetate, citrate, maleate, malate, or mesylate. Preferred salts include hydrofluoric, hydrochloric, hydrobromic, hydroiodic, acetate, citrate, maleate, or mesylate. More preferred salts include hydrochloric, acetate, or maleate.

The salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of an existing salt for another ion or suitable ion-exchange resin.

The compounds used in the methods of the invention were synthesized using the methodology described in U.S. Pat. Nos. 8,592,465; 8,822,513; 9,029,408; 9,334,242; 9,447,049; and 10,301,285 and US publication No. 2020/24270, hereby incorporated by reference.

Pharmaceutical Composition

The methods of the invention include the administration of a pharmaceutical composition including a pharmaceutically acceptable carrier and at least one compound described herein. Typically, the pharmaceutical composition may include a compound or its pharmaceutically acceptable salt, and at least one pharmaceutically acceptable excipient. The term "pharmaceutically acceptable excipient" refers to any suitable adjuvants, carriers, excipients, flavorant, or stabilizers, and can be used in pharmaceutical formulations either in solid or liquid form. Such forms include, but are not limited to, tablets, capsules, powders, solutions, suspensions, or emulsions.

The amount of compound used in the method and the dosage regimen for treating a disease condition depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods.

Typically, the formulations have from about 0.01 to about 99 percent by weight of at least one compound by weight, preferably from about 20 to 75 percent of active compound(s), together with the adjuvants, carriers and/or excipients. While individual needs may vary, determination of optimal ranges of effective amounts of each component is within the skill of the art. Typical daily dosages include about 2 mg to about 200 mg or about 1 mg to about 100 mg, preferred daily dosages include about 4 mg to about 90 mg, and the most preferred dosages include about 4 mg to about 80 mg of the compound. Other preferred dosages include the anti-inflammatory compound in an amount of about 4 mg to about 45 mg, or 9 mg to about 18 mg. Alternatively, a dose is from about 0.01 to 150 mg/kg body weight, preferably from about 1 mg to about 100 mg/kg body weight, and more preferably from about 2 to 50 mg/kg body weight, may be appropriate. The daily dose can be administered in one to four doses per day. Treatment regimen for the administration of the compounds of the present invention can also be determined readily by those with ordinary skill in art. That is, the frequency of administration and size of the dose can be established by routine optimization, preferably while minimizing any side effects.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a subject's condition, a maintenance dose of a compound, composition or formulation may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The methods may include "additional therapeutic agents" including, but are not limited to, nonsteroidal anti-inflammatory drugs (NSAIDs) such as celecoxib, diclofenac, diflunisal, etodolac, etoricoxib, fenoprofen, flurbiprofen, ibuprofen, indomethacin, ketoprofen, ketorolac, mefenamic acid, meloxicam, nabumetone, naproxen, oxaprozin, piroxicam, sulindac, tolmetin, and the like; Cox-2 selective agents such as celecoxib, rofecoxib, and valdecoxib; salicylates such as acetylated salicylates like aspirin and or non-acetylated salicylates like salsalate; also anti-pyretic analgesics like acetaminophen. Corticosteroidal anti-inflammatory agents (corticosteroids) such as betamethasone, dexamethasone, deflazacort, fludrocortisone, hydrocortisone and derivatives, methylprednisone, prednisolone, prednisone, triamcinolone, alclometasone, alclometasone dipropionate, amcinonide, beclomethasone, beclomethasone dipropionate, budesonide, ciclesonide, clobetasol, clobetasol propionate, clocortolone, clocortolone pivalate, desonide, desoximetasone, diflorasone, diflorasone diacetate, flunisolide, fluocinolone acetonide, fluocinonide, fluorometholone, fluprednisolone, flurandrenolide, fluticasone, fluticasone propionate, halcinonide, halobetasol, halobetasol propionate, mometasone, mometasone furoate, paramethasone, prednicarbate, triamcinolone acetonide, and the like. Biological anti-inflammatory agents such as tumor necrosis factor inhibitors (TNFi) including adalimumab, certolizumab pegol, etanercept, golimumab, infliximab, and non-TNFi agents such as abatacept, anakinra, rituximab, and tocilizumab. Traditional disease modifying antirheumatic drugs such as baricitinib, chloroquine, hydroxychloroquine, leflunomide, methotrexate, sulfasalazine, tofacitinib, and the like. Agents to treat gout such NSAIDs and corticosteroids as listed above, colchicine binding site inhibitors such as colchicine and the like, xanthine oxidase inhibitors such as allopurinol and febuxostat, and the like; uricouric agents such as lesinurad, probenecid, sulfinpyrazone and the like.

The methods of the invention may be administered in conjunction with other anti-inflammatory therapies to treat inflammation, e.g., combination therapy. Suitable agents contemplated for use in combination with the methods of the invention may include nonsteroidal anti-inflammatory drugs (NSAIDs) such as celecoxib, diclofenac, diflunisal, etodolac, etoricoxib, fenoprofen, flurbiprofen, ibuprofen, indomethacin, ketoprofen, ketorolac, mefenamic acid, meloxicam, nabumetone, naproxen, oxaprozin, piroxicam, sulindac, tolmetin, and the like; Cox-2 selective agents such as celecoxib, rofecoxib, and valdecoxib; salicylates such as acetylated salicylates like aspirin and or non-acetylated salicylates like salsalate; also anti-pyretic analgesics like acetaminophen. Corticosteroidal anti-inflammatory agents (corticosteroids) such as betamethasone, dexamethasone, deflazacort, fludrocortisone, hydrocortisone and derivatives, methylprednisone, prednisolone, prednisone, triamcinolone, alclometasone, alclometasone dipropionate, amcinonide, beclomethasone, beclomethasone dipropionate, budesonide, ciclesonide, clobetasol, clobetasol propionate, clocortolone, clocortolone pivalate, desonide, desoximetasone, diflorasone, diflorasone diacetate, flunisolide, fluocinolone acetonide, fluocinonide, fluorometholone, fluprednisolone, flurandrenolide, fluticasone, fluticasone propionate, halcinonide, halobetasol, halobetasol propionate, loteprednol etabonate, mometasone, mometasone furoate, paramethasone, prednicarbate, triamcinolone acetonide, and the like. Biological anti-inflammatory agents such as tumor necrosis factor inhibitors (TNFi) including adalimumab, certolizumab pegol, etanercept, golimumab, infliximab, and non-TNFi agents such as abatacept, anakinra, rituximab, and tocilizumab. Traditional disease modifying antirheumatic drugs such as baricitinib, chloroquine, hydroxychloroquine, leflunomide, methotrexate, sulfasalazine, tofacitinib, and the like. Agents to treat gout such NSAIDs and corticosteroids as listed above, colchicine binding site inhibitors such as colchicine and the like, xanthine oxidase inhibitors such as allopurinol and febuxostat, and the like; uricouric agents such as lesinurad, probenecid, sulfinpyrazone and the like; and agents that enhance the degradation of uric acid such as pegloticase and the like.

When the inflammation is caused by a virus the method may include an antiviral therapy such as a neuraminidase inhibitor, remdesivir, hydroxychloroquine, azithromycin, or hemagglutinin inhibitor. Other therapies included in the methods are medications that modulate the immune system or host cell factors such as dexamethasone; corticosteroids; an IL-6 inhibitor such as tocilizumab; interferons; an IL-1 inhibitor; or a kinase inhibitor such as baricitinib. The methods may further comprise an antibody therapy such as high titer COVID-19 convalescent plasma, IVIG, a monoclonal antibody therapy such as casirivimab plus imdevimab, bamlanivimab, or bamlanivimab plus etesevimab. The methods may further comprise tocilizumab or baricitinib. The methods may further comprise an additional therapy such as high titer COVID-19 convalescent plasma; IVIG; casirivimab plus imdevimab; bamlanivimab; or bamlanivimab plus etesevimab. The methods may include a second antiviral therapy that is at least one of favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanarnivir, or valacyclovir. The methods may include a second therapy that is at least one of vitamins C or D, zinc, famotidine, ivermectin, or angiotensin converting enzyme inhibitor (ACEI) or angiotensin receptor binding (ARB) agent.

The solid unit dosage forms can be of the conventional type. The solid form can be a capsule and the like, such as an ordinary gelatin type containing the compounds and a carrier. Carriers include, but are not limited to, lubricants and inert fillers such as, castor oil and similar materials, lactose, sucrose, or cornstarch. The formulations may be tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

The invention can be mixed at cold temperatures, room temperature, or elevated temperatures with a liquid carrier such as a fatty oil, castor oil, or other similar oil to manufacture tablets, capsules, and the like.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the formulation may include excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Typical compositions according to the present invention are prepared so that an oral dosage unit contains between about 1 mg and 100 mg of active compound, and preferred oral compositions contain between 1 mg and 50 mg of active compound.

The formulations may be orally administered with an inert diluent, or with an assimilable edible carrier, or they can be enclosed in hard or soft shell capsules, or they can be compressed into tablets, or they can be incorporated directly with the food of the diet. A preferred formulation is an oral formulation.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions used in the method of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

The formulation may also be administered parenterally. Solutions or suspensions of these formulations can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the formulations may be in solution or suspension may be packaged in a pressurized aerosol container together with suitable propellants, for example, hydrocarbon propellants like propane, butane, or isobutane with conventional adjuvants. The formulations also may be administered in a non-pressurized form such as in a nebulizer or atomizer.

When administering the formulations in the methods of the invention, the formulations may be administered systemically or sequentially. Administration can be accomplished in any manner effective for delivering the compounds or the pharmaceutical compositions to the site of inflammation. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

The invention is directed to methods of treating inflammation with the compounds and formulations described above. The compounds and formulations thereof have utility in treating inflammation by disrupting tubulin polymerization. The formulations may optionally comprise additional active ingredients, whose activity is useful for treating diseases associated with inflammation, treat adverse effect associated with the compounds or dosages of a particular formulation, and/or delay or extend the release of the ingredients. A series of experiments examined the ability of compounds of this invention such as compound 17ya to inhibit the inflammasome reaction. The experiment here is the IL-1β study performed in THP-1 cells (Example 4). These cells are human derived and are designed to study the signals involved in inflammasome activation. To become susceptible to inflammasome inducers, these cells must be induced by stimuli which in this case was phorbol 12-myristate acetate (PMA). Colchicine is an important comparator in these studies since colchicine is known to be an anti-inflammatory compound. Colchicine prevents microtubule assembly and thereby disrupts inflammasome activation, microtubule-based inflammatory cell chemotaxis, generation of leukotrienes and cytokines, and phagocytosis. Colchicine is also utilized clinically for this application.

IL-1β is one of the key modulators of inflammation and a direct readout of the inflammasome complex. Specifically, the NLRP3 inflammasome. In this study, Applicants demonstrated that THP-1 cells that are stimulated by the pro-inflammatory compound, nigericin, produce more IL-1β, than the untreated cells. Microtubule disruptors compound 17ya (labeled as Veru) and colchicine both dose-dependently (partially) suppressed the IL-1β levels induced by nigericin. Further, in comparison to colchicine, compound 17ya had a much greater effect (higher efficacy and potency) in inhibiting IL-1β. Again, in this model, the secretion of IL-1β is an indicator of the inflammasome reaction and therefore the reduction in expression is indicative of an inhibition of the inflammasome reaction. Given these data, compounds of the invention work to treat patients with a wide variety of diseases and conditions with an inflammatory component as described herein and further as known by the skilled artisan.

In a complementary study (Example 3), the expression of another of the inflammasome modulators, TNF-α, was studied. TNF-α has been shown to be an activator of the inflammasome reaction. In this study, spleen cells from mice were activated with lipopolysaccharide (LPS). In this study, compound 17ya reduced the expression of TNF-α approximately 40%, a similar magnitude as the known inflammatory modulator, colchicine. When the compounds of the invention are administered to a patient suffering from inflammation, the compounds typically reduce TNF-α from about 15% to 60%, preferably from about 25% to 50%, and more preferably from about 30% to 45%. Similarly, when compounds of the invention are administered to patients suffering from inflammation, the compounds typically the reduction of IL-1β is about 10% to 30%, and preferably about 15% to 25%, alternatively depending on the conditions, the reduction may be about 80% to 98%, preferably 85% to 95%.

Another in vitro study (Example 2) was conducted to determine if compounds of the invention can suppress toxic shock levels of these key cytokines of the cytokine storm. In particular, the effects of compound 17ya on cytokine production was assessed by stimulating isolated mouse spleen cells with an microbial endotoxin that causes septic shock called lipopolysaccharide (LPS) (Example 2). The cells were stimulated with 5 μg/ml LPS for 1 hour and then incubated overnight (approximately 21 hours) with compound 17ya to mimic the clinical situation, and thereafter, the cytokine levels were analyzed.

At a concentration that represents the blood levels of compound 17ya observed in clinically dosed patients, compound 17ya (40 nM) significantly reduced the production of key cytokines known to be involved with COVID-19 cytokine storm: TNFα (−31%) ($p=0.006$), IL-1α (−123%) ($p=0.0005$), IL-1β (−97%) ($p=0.0003$), IL-6 (−85%) ($p<0.00008$), and IL-8 homologue (−96%) ($p<0.0000007$). This reduction was similar to, or greater than, depending on the specific cytokine, to that observed with dexamethasone (10 nM), a steroid and a known inhibitor of cytokine production during inflammation. Given these data, it is expected that compounds of the invention would also work to treat patients with inflammation arising from other indications.

Suppression of these key cytokines (especially, IL-1β and IL-18) by preventing the assembly and activation of the inflammasome may be an effective way to prevent clinical deterioration of patients with COVID-19 to ARDS or to treat COVID-19 patients with ARDS, or to treat a wide variety of other inflammatory diseases as discussed herein and as known by the skilled artisan. A double-blind randomized (1:1) placebo-controlled Phase 2 clinical trial evaluating daily oral doses of compound 17ya versus placebo for 21 days in 40 hospitalized patients who tested positive for the SARS-CoV-2 virus and are at high risk for ARDS was performed (Example 1). The primary efficacy endpoint was the proportion of patients that are alive and without respiratory failure at Day 22. Secondary endpoints include the measured improvements on the WHO Disease Severity Scale (8-point ordinal scale) which captures COVID-19 disease symptoms and signs including hospitalization to progression of pulmonary symptoms to mechanical ventilation as well as death. Compound 17ya was shown to improve proportion of subjects alive and free of respiratory failure (Table 2), days on mechanical ventilator and in ICU (Table 3 and [00138]-[00139]), and treatment failure at day 29 and day 15 (see [00136]-[00137]), with a side effect profile that suggests that compound 17ya was well tolerated.

Blocking IL-1, particularly IL-1β, is now the standard of therapy for a class of inflammatory syndromes termed "autoinflammatory" diseases (reviewed by Simon and van der Meer; and Masters et al). Autoinflammatory syndromes are distinct from autoimmune diseases. In autoimmune diseases, the T cell is associated with pathogenesis as the dysfunctional cell or "driver" of inflammation. Immunosuppressive therapies targeting T-cell function as well as antibodies that deplete T and B cells are effective in treating autoimmune diseases. In contrast, in autoinflammatory diseases, the monocyte-macrophage is the dysfunctional cell, which directly promotes inflammation. Autoinflammatory conditions are characterized by recurrent bouts of fever with debilitating local and systemic inflammation; they are often responsive to IL-1β blockade (Table 1). In general, these diseases are poorly controlled with immunosuppressive therapies, and responses to blocking TNFα, if any, are modest. Examples of diseases responsive to bBlocking IL-1β as treatment of acute and chronic inflammatory diseases includes such classic autoinflammatory diseases as familial Mediterranean fever (FMF), pyogenic arthritis, pyoderma gangrenosum, acne (PAPA), cryopyrin-associated periodic syndromes (CAPS), hyper IgD syndrome (HIDS), adult and juvenile Still disease, Schnitzler syndrome, TNF receptor-associated periodic syndrome (TRAPS), Blau syndrome, Sweet syndrome, deficiency in IL-1 receptor antagonist (DIRA), recurrent idiopathic pericarditis, macrophage activation syndrome (MAS), urticarial vasculitis, antisynthetase syndrome, relapsing chondritis, Behcet disease, Erdheim-Chester syndrome (histiocytosis), and [synovitis, acne, pustulosis, hyperostosis, osteitis (SAPHO)]. Common diseases mediated by IL-1β include Rheumatoid arthritis; Periodic fever, aphthous stomatitis, pharyngitis, adenitis syndrome (PFAPA); Urate crystal arthritis (gout); Type 2 diabetes; Smoldering multiple myeloma; and Postmyocardial infarction heart failure.

Inflammatory Methods of the invention may be used to treat inflammation caused by the following diseases including, but not limited to, chronic inflammatory diseases and autoimmune diseases. Examples include virally induced inflammation, arthritis, gout, acute respiratory distress syndrome (ARDS), systemic acute respiratory syndrome (SARS), allergies, Alzheimer's disease, asthma, autoimmune diseases, cardiovascular disease, cancer, chronic obstructive pulmonary disease, coeliac disease, Crohn's disease, diabetes type I, diabetes type II, endometriosis, fatty liver disease, glomerulonephritis, hepatitis, inflammatory bowel disease, multiple sclerosis, muscular dystrophies such as Duchenne muscular dystrophy, obesity, Parkinson's disease, periodontitis, psoriasis, rheumatoid arthritis, sinusitis, tuberculosis, ulcerative colitis. a) prevention, treatment, or reversal of arthritis; b) prevention, treatment, or reversal of an arthritic condition such as Behcet's disease (autoimmune vasculitis), bursitis, calcium pyrophosphate dihydrate crystal (CPPD), deposition disease (or pseudogout), carpal tunnel syndrome, connective tissue disorders, Crohn's diseases, Ehlers-Danlos syndrome (EDS), fibromyalgia, gout, infectious arthritis, inflammatory bowel disease (IBD), juvenile arthritis, systemic lupus erythematosus (SLE), Lyme's disease, Marfan syndrome, myositis, osteoarthritis, polyarteritis nodosa, polymyalgia rheumatica, psoriasis, psoriatic arthritis, Raynaud's phenomenon, reflex sympathetic dystrophy syndrome, Reiter's syndrome, rheumatoid arthritis, scleroderma, Sjogrens' syndrome, tendonitis or ulcerative colitis; c) preventing, treatment, or reversing an autoimmune disease.

Methods of the invention may be used to treat inflammation caused by viruses including those of the superfamilies of Coronaviridae. Also, the methods of the invention may be used to treat inflammation caused by viruses including SARS-CoV, MERS-CoV, or COVID-19.

The methods of the invention may be used to treat inflammation caused by SARS-CoV, MERS-CoV, or SARS-CoV-2, and in particular SARS-CoV-2 infection. The methods of the invention may be used to treat subjects with SARS-CoV-2 infection at high risk for acute respiratory distress syndrome (ARDS) or severe acute respiratory syndrome (SARS). The subject may have a SARS-CoV-2 infection that reduces mortality. Another embodiment of the invention encompasses methods wherein treating a subject with SARS-CoV-2 infection at high risk for acute respiratory distress syndrome (ARDS) or severe acute respiratory syndrome (SARS) reduces mortality. Another embodiment of the invention encompasses methods wherein treating a subject with SARS-CoV-2 infection reduces morbidity. Another embodiment of the invention encompasses methods wherein treating a subject with SARS-CoV-2 infection at high risk for acute respiratory distress syndrome (ARDS) or severe acute respiratory syndrome (SARS) reduces morbidity. Another embodiment of the invention encompasses methods wherein treating a subject with SARS-CoV-2 infection reduces respiratory failure, days in ICU, days on mechanical ventilator, or improves WHO Ordinal Scale for Clinical Improvements. Another embodiment of the invention encompasses methods wherein treating a subject with SARS-CoV-2 infection at high risk for acute respiratory distress syndrome (ARDS) or severe acute respiratory syndrome (SARS) reduces respiratory failure, days in ICU, days on mechanical ventilator, or improves WHO Ordinal Scale for Clinical Improvements. Another embodiment of the invention encompasses methods wherein treating a subject with SARS-CoV-2 infection reduces mortality or respiratory failure in subjects>60 years of age. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure in subjects>60 years of age. Another embodiment of the invention encompasses methods wherein treating a subject with SARS-CoV-2 infection reduces mortality or respiratory failure when dosed in combination with remdesivir and/or dexamethasone. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure when dosed in combination with remdesivir and/or dexamethasone.

The invention encompasses methods for treating inflammation in a subject in need thereof comprising administering to the subject a formulation having a compound described herein or a pharmaceutically acceptable salt, hydrate, polymorph, or isomer thereof in a therapeutically effective amount to treat the inflammation. The methods include at least one of compound 12db, compound 11 cb, compound 11 fb, compound 12da, compound 12fa, compound 12fb, compound 12cb, compound 55, compound 66a, or compound 17ya. In a particular method, the method includes compound 17ya.

As used herein unless otherwise stated, the term "subject or patient" refers to any mammalian patient, including without limitation, humans, other primates, dogs, cats, horses, cows, sheep, pigs, rats, mice, and other rodents. In particular, the subject is a human, and alternatively may be only male or only female.

When administering the compounds and formulations described herein, the formulations can be administered systemically or directly to a specific site where the inflammation is present. Administration may be accomplished in any manner effective for delivering the compounds or the pharmaceutical compositions to the inflammation site. Administration methods include, but are not limited to, oral, topical, transdermal, parenteral, subcutaneous, intravenous, intramuscular, intraperitoneal, intranasal, by intracavitary or intravesical instillation, intraocular, intraarterial, intralesional, or by application to the mucous membrane. Mucous membranes include those found in the nose, throat, and/or bronchial tubes, among others. Preferably, the formulation is administered orally. Administration may be simultaneous or sequential with additional anti-inflammation compounds or formulations, or treatments used to address side effects associated with the compounds or dosages.

The following examples are presented in order to more fully illustrate the preferred embodiments of the invention. They should in no way, however, be construed as limiting the broad scope of the invention.

EXAMPLES

The Examples set forth below are for illustrative purposes only and are not intended to limit, in any way, the scope of the present invention.

Materials and Methods

In Vitro Tubulin Polymerization Assay. Bovine brain tubulin (0.4 mg, >97% pure) (Cytoskeleton, Denver, CO) was mixed with 10 μM of the test compounds and incubated in 100 μL of general tubulin buffer (80 mM PIPES, 2.0 mM $MgCl_2$, 0.5 mM EGTA, and 1 mM GTP) at pH 6.9. The absorbance of wavelength at 340 nm was monitored every 1 min for 20 min by the SYNERGY 4 Microplate Reader (Bio-Tek Instruments, Winooski, VT). The spectrophotometer was set at 37° C. for tubulin polymerization.

Isolation and culture of mouse spleen cells in Example 2. Spleen cells were isolated from 10-weeks old tight skin 1 Vitamin D deficient (TSK1 D−) female mice and cultured with RPMI-1640 medium with 10% FBS. $2\times10^6$ cells per well were plated in 24-well plates and subsequently stimulated with 5 μg/mL LPS for 1 hour. Different concentrations of compound 17ya and dexamethasone were added to the plate and incubated at 37° C. and 5% $CO_2$ in a humidified atmosphere overnight.

Cytokine measurement by ELISA in Example 2. Multiple cytokines level (TNF-α, IL-1α, L-1β or IL-6 and CXCL1/KC) in cell culture supernatants from mouse spleen cells were determined by enzyme-linked immunosorbent assay (ELISA) kit (Quantikine) for mouse cytokines according to manufacturer's instruction (R&D Systems, Minneapolis, MN). Briefly, 50 μL of the Assay Diluent was added to each well of a 96-well culture plate followed by 50 μL of culture supernatant samples. The plate was incubated for 2 hours at room temperature. The supernatants in each well were aspirated and washed five times with Wash Buffer (400 μL) using an autowasher. 100 μL conjugate solution was then added in each well and incubated for 2 hours at room temperature. Repeated the washing steps, after which 100 μL Substrate Solution was added into each well and incubated for 30 min at room temperature. The reaction stopped when 100 μL Stop Solution was added. The optical density (OD) of each well was determined at 450 nm using a microplate reader and the cytokines level were evaluated.

Example 1

Treatment of Inflammation in Subjects With COVID-19

Efficacy: Described in this example are the results of a clinical trial (COVID-19 study) that was a Phase 2, double-blind, placebo-controlled, proof-of-concept study of approximately 40 hospitalized patients with COVID-19 at high risk for acute respiratory distress syndrome (ARDS). The primary endpoint of this study was the proportion of patients alive without respiratory failure at Day 29. Key secondary endpoints include the following: proportion of patients alive without respiratory failure at Day 15 and Day 22, all-cause mortality, days in intensive care unit (ICU), and days on mechanical ventilation. A summary of the efficacy observations in the intent to treat (ITT) population from this study are listed below. The p-values presented are from a chi-square analysis for responder analysis and t-test for continuous variables. Please note that no a was set in the Phase 2 study, however for small studies such as this, the α is generally set at 0.1. Therefore, any p-value<0.1 is considered statistically significant.

This protocol employed a responder analysis. A group of 39 subjects hospitalized for COVID-19 infection at high risk for acute respiratory distress syndrome (ARDS) were divided into two groups, a placebo group of 20 subjects and a treated group (group treated with compound 17ya) of 19 patients. The treated group was given a powder filled capsule containing 18 mg of compound 17ya taken by mouth daily until hospital discharge, up to a maximum of 21 days of dosing.

These hospitalized subjects were qualified as responders if they were alive without respiratory failure on Day 15, Day 22, and Day 29. A non-responder is a subject that EITHER died before the analysis day OR had respiratory failure on the analysis day. After a subject was discharged/deceased, to establish responder/non-responder status, a phone call was made to see if the subject was alive and had no evidence of respiratory failure on Day 15, Day 22, and Day 29 and in the safety follow-up of the study. For example, if a patient died on Day 8, they were a non-responder at Day 15, Day 22, and Day 29. If a patient had respiratory failure on Day 15, but not on Day 22 or Day 29, they would be a non-responder on Day 15, but not on Day 22 or Day 29. For this analysis, "all-cause mortality" was evaluated and anyone who died was taken as a non-responder. Responders also included subjects who were discharged from the hospital or have Grade 0-4 on the WHO Ordinal Scale for Clinical improvement on Day 15, Day 22, or Day 29 (evaluation day), and non-responders were subjects who died before the evaluation day or had Grade 5-8 on the WHO Ordinal Scale for Clinical Improvement on the evaluation day.

Primary endpoint: Compound 17ya reduced the proportion of patients that are non-responders, i.e., death or respiratory failure from 35.0% in the placebo group (7/20) to 15.8% (3/19) in the compound 17ya treated group at Day 15 (p=0.1697) and from 30.0% (6/20) in the placebo group to 10.5% (2/19) in the compound 17ya treated group at Day 29 (p=0.1322). See Table 2. This represents an approximately 55% reduction in treatment failures at Day 15 and a 65% reduction in treatment failures at Day 29 in the compound 17ya treated group compared to placebo.

TABLE 2

Proportion of subjects alive and free of respiratory failure by visit (ITT population)

| | Response | 17ya (n = 19) | Placebo (n = 20) | Odds ratio/95% CI/p-value |
|---|---|---|---|---|
| Day 15 | Responder | 16 (84.2%) | 13 (65.0%) | 2.56/(0.38, |
| | Non-responder | 3 (15.8%) | 7 (35.0%) | 17.23)/0.3342 |
| Day 22 | Responder | 16 (84.2%) | 14 (70.0%) | 2.14/(0.31, |
| | Non-responder | 3 (15.8%) | 6 (30.0%) | 14.88)/0.4433 |
| Day 29 | Responder | 17 (89.5%) | 14 (70.0%) | 2.69/(0.36, |
| | Non-responder | 2 (10.5%) | 6 (30.0%) | 20.39)/0.3379 |

Compound 17ya reduced the proportion of patients who died up to 60 days after initiation of treatment from 30% (6/20) in the placebo group to 5% (1/19) in the compound 17ya treated group. This is an approximately 82% reduction in mortality in the compound 17ya treated group.

Compound 17ya reduced the days on mechanical ventilation from an average of 5.4 days in the placebo group to 1.6 days in the compound 17ya treated group. This represents a 3.4-fold increase in the days on mechanical ventilation in the placebo group compared to the compound 17ya treated group. See Table 3.

Compound 17ya reduced the days in ICU from an average of 9.6 days in the placebo group to 3.0 days in the compound 17ya treated group. This represents a 3.2-fold increase in the days in the ICU in the placebo group compared to the compound 17ya treated group. See Table 3.

TABLE 3

| Treatment | N | Mean | SD | P-value |
|---|---|---|---|---|
| Days on Mechanical Ventilation | | | | |
| Compound 17ya | 19 | 1.6 | 6.64 | 0.4836 |
| Placebo | 20 | 5.4 | 10.16 | |
| Days in ICU | | | | |
| Compound 17ya | 19 | 3.0 | 7.16 | 0.0742 |
| Placebo | 20 | 9.6 | 11.54 | |

FIG. 1 illustrates the mean WHO Ordinal Scale for Clinical Improvement by Day (0=baseline). The area under the mean curve (AUC) is 153 in the group treated with compound 17ya and AUC is 182 in the Placebo group, indicating greater morbidity in the placebo population and suggesting a clinical improvement associated with receiving compound 17ya.

As the study was limited in sample size based on FDA comments received during the IND review process, the study sponsor (Veru) has conducted post-hoc, sub-group analyses of the data from the study. The following additional observations are made from this study:

In the compound 17ya treated group there was one patient who was noncompliant with oxygen supplementation. This patient was noncompliant with standard of care in this study. An analysis of the primary endpoint excluding this patient (MITT population) from the analysis shows a 30% failure rate in the Placebo group (same as Table 2) compared to a 5.6% failure rate in the compound 17ya treated group at Day 29 (lower than in Table 2). This represents an 81% reduction in treatment failures.

It is well recognized that older patients are at higher risk for death and respiratory failure in patients with COVID-19 compared to younger patients. In an analysis of treatment failures in patients>60 years of age showed that a statistically significant and clinically meaningful reduction in treatment failures were observed in the compound 17ya treated group compared to placebo in this high-risk population.

| | N | Treatment failures at Day 29 | p-value |
|---|---|---|---|
| Compound 17ya | 11 | 1 (9%) | 0.0456 (chi-square) |
| Placebo | 8 | 4 (50%) | |

A risk factor for an adverse clinical outcome in a patient with COVID-19 is the severity of disease at presentation. To assess this risk factor, an analysis of patients with a WHO Score of Disease Severity≥5 at baseline was performed. The outcome of this analysis shows a statistically significant and clinically meaningful reduction in treatment failures were observed in the compound 17ya treated group compared to placebo in this high-risk population. Also, clinically meaningful reduction (78%; not shown) in mortality was observed in the compound 17ya treated (1/10 or 10%) group compared to placebo (6/13 or 46%) in this high risk population.

| | N | Treatment failures at Day 15 | p-value |
|---|---|---|---|
| Compound 17ya | 9* | 1 (11%) | 0.0827 (chi-square) |
| Placebo | 13 | 6(46%) | |

*one patient in the compound 17ya treated group was noncompliant with oxygen therapy and is excluded from this modified intent to treat (MITT) analysis.

An analysis of the days in ICU in evaluable patients showed a statistically significant and clinically meaningful reduction in days in ICU in the compound 17ya treated group compared to placebo.

| | N | Mean days in ICU (±st. dev) | p-value |
|---|---|---|---|
| Compound 17ya | 18 | 3.00 ± 7.37 | 0.0469 (t-test) |
| Placebo | 20 | 9.55 ± 12.56 | |

Additionally, the proportion of patients that were in the ICU for ≥3 days on study is statistically significantly higher in the placebo group compared to the compound 17ya treated group.

| | N | Treatment failures at Day 29 | p-value |
|---|---|---|---|
| Compound 17ya | 18 | 4 (22%) | 0.0390 (chi-square) |
| Placebo | 20 | 11 (55%) | |

In this study, patients were permitted to receive standard of care. At the time of the study, the standard of care included treatment with remdesivir and/or dexamethasone under an Emergency Use Authorization. There were eleven patients in the study that did not receive either remdesivir or dexamethasone (6 in the compound 17ya treated group and 5 in the placebo group). An analysis of patients that received the recognized standard of care was conducted. Specifically, the days in ICU and the days on mechanical ventilation were compared between the treatment groups. In this population, in patients that received standard of care, no patient treated with compound 17ya required admission in the ICU or mechanical ventilation and there were no mortalities in this patient group. In the placebo group, 53% (8/16) required ICU admission with an average of 9.5 days in the ICU, 20% (3/15) required mechanical ventilation with an average of 3.9 days of mechanical ventilation, and 27% (4/15) died on study.

Overall, the study sponsor proposes that compound 17ya shows strong clinically meaningful outcomes in this small, proof-of-concept, Phase 2 study with statistically significant observations in reductions in death in the ITT population and in post-hoc, high-risk sub-group analyses, and days in ICU. It is important to note that all the parameters measured in the study show clinically meaningful outcomes with compound 17ya compared to placebo and there are no parameters that do not indicate benefit with compound 17ya treatment compared to placebo although some parameters do not reach statistical significance in this small study.

Safety: The overall safety conclusions are: (1) There were no treatment related serious adverse events observed on the study; (2) There were no treatment related adverse events observed on the study; and (3) The treatment emergent adverse events that were observed in at least 2 patients in either treatment group in the study are presented in Table 4. There is no imbalance against compound 17ya in adverse events observed in the study.

TABLE 4

COVID-19 Study: Treatment Emergent Adverse Events Observed in ≥2 Patients in Either Treatment Group by Preferred Term

| Preferred Term | Compound 17ya 18 mg (n = 19) N (%)/events | Placebo (n = 20) N (%)/events |
|---|---|---|
| Any | 10 (52.6)/27 | 11 (55.0)/41 |
| Constipation | 2 (10.5)/2 | 2 (10.0)/2 |
| Septic shock | 1 (5.3)/1 | 2 (10.0)/2 |
| Alanine aminotransferase increased | 1 (5.3)/1 | 2 (10.0)/2 |
| Aspartate aminotransferase increased | 2 (10.5)/2 | 1 (5.0)/1 |
| Acute kidney injury | 0 | 2 (10.0)/2 |
| Pneumomediastinum | 0 | 2 (10.0)/2 |
| Pneumothorax | 1 (5.3)/1 | 3 (15.0)/3 |
| Respiratory failure | 0 | 4 (20.0)/4 |

The treatment emergent serious adverse events observed in the study are presented in Table 5. There is no imbalance against compound 17ya in serious adverse events observed in the study.

TABLE 5

COVID-19 Study: Serious Adverse Events Observed by System Organ Class and Preferred Term

| System Organ Class Preferred Term | Compound 17ya 18 mg (n = 19) N (%)/events | Placebo (n = 20) N (%)/events |
|---|---|---|
| Any | 3 (15.8)/3 | 4 (20.0)/4 |
| Cardiac disorders | 1 (5.3)/1 | 0 |
| Cardiac arrest | 1 (5.3)/1 | 0 |
| Infections and infestations | 1 (5.3)/1 | 2 (10.0)/2 |
| COVID-19 | 0 | 1 (5.0)/1 |
| Septic shock | 1 (5.3)/1 | 1 (5.0)/1 |
| Nervous system disorders | 0 | 1 (5.0)/1 |
| Encephalopathy | 0 | 1 (5.0)/1 |
| Renal and urinary disorders | 0 | 1 (5.0)/1 |
| Acute kidney injury | 0 | 1 (5.0)/1 |
| Respiratory, thoracic and mediastinal disorders | 1 (5.3)/1 | 2 (10.0)/2 |
| Epistaxis | 1 (5.3)/1 | 0 |
| Respiratory failure | 0 | 2 (10.0)/2 |

Overall, compound 17ya was well tolerated in this patient population with no clinically relevant safety observations in the compound 17ya treated group. The data in Example 1 support the treatment of coronaviruses with compounds of this invention with a likely contribution to efficacy in the ability of the invention compounds to exert anti-inflammatory effects via suppression of multiple cytokines (Example 2) and specifically TNF-α (Example 3) and IL-1β, supporting the ability to suppress inflammasome activity in vivo, including in late stage coronavirus infections.

Example 2

Treatment of Inflammation by Suppression of Inflammasome Activity

Overall, compound 17ya was well tolerated in this patient population with no clinically relevant safety observations in the compound 17ya treated group.

Interleukin (IL)-1β cytokine that is a key mediator of antiviral immunity. The production of IL-1β requires transcription by innate immune receptor signaling and as well as the maturational cleavage by the multi-molecular inflammasome complex. Therefore, IL-1β is a key indicator of inflammasome activity. IL-1β then goes on to activate antiviral process and adaptive immune responses. Therefore, suppression of IL-1β serves as a measurement of anti-inflammasome activity.

An in vitro study was conducted to determine if compound 17ya can suppress toxic shock levels of these key cytokines of the cytokine storm. The effects of compound 17ya on cytokine production was assessed by stimulating isolated mouse spleen cells with an endotoxin that causes shock called lipopolysaccharide (LPS). Stimulating isolated mouse spleen cells with an endotoxin (lipopolysaccharide (LPS)) results in activation of the inflammasome complex in the cells. The cells were stimulated with 5 μg/ml LPS for 1 hour and then incubated overnight (approximately 21 hours) with compound 17ya at a 40 nM concentration that represents the blood levels of compound 17ya observed in clinically dosed patients to mimic the clinical situation, and cytokine levels were analyzed. This treatment significantly reduced the production IL-1β (−123%) (p=0.0005) the central hallmark of inflammasome induction. At a concentration that represents the blood levels of compound 17ya observed in clinically dosed patients, compound 17ya (40 nM) significantly reduced the production of several key cytokines known to be involved with COVID-19 cytokine storm: TNFα (−31%) (p=0.006) (Table 2), IL-1α (−123%) (p=0.0005) (Table 6), IL-1β (−123%) (p=0.0005) (Table 5), IL-6 (−85%) (p<0.00008) (Table 3), and CXCL-1/KC (i.e., IL-8 homologue) (−96%) (p<0.0000007) (Table 4). In Tables 2-6, the column headings 1, 2, and 3 mean three replicates of each sample. In each table the top data set are raw data, whereas the bottom set of data are adjusted data by subtracting the average value of the control from the top data set. Table 7 is a comparison of the average cytokine suppression achieved by compound 17ya vs dexamethasone (Dex) for each cytokine listed above.

Compound 17ya (40 nM) significantly reduced the production IL-1β that is the central hallmark of inflammasome induction. These cytokines are produced by virus activated inflammasomes; hence, reduction in levels of these cytokines is consistent with 17ya decreasing the activity of inflammasomes. This reduction was similar to, or greater than, depending on the specific cytokine, to that observed with dexamethasone (10 nM), a steroid and a known inhibitor of cytokine production during inflammation.

Data obtained from the isolated mouse spleen cells is as follows.

TABLE 2

TNF-α

| | 1 | 2 | 3 | Average | Std Deviation |
|---|---|---|---|---|---|
| Control | 0.625 | 0.816 | 2.113 | 1.18 | 0.66 |
| LPS | 165.924 | 143.463 | 161.1 | 156.83 | 9.65 |
| Compound 17ya | 100.118 | 116.04 | 109.155 | 108.44 | 6.52 |
| Dex 10 nM | 35.478 | 32.494 | 32.825 | 33.60 | 1.34 |
| LPS | 164.739 | 142.278 | 159.915 | 155.644 | |
| Compound 17ya | 98.933 | 114.855 | 107.970 | 107.253 | |
| Dex 10 nM | 34.2933 | 31.309 | 31.640 | 32.414 | |

TABLE 3

IL-6

| | 1 | 2 | 3 | Average | Std Deviation |
|---|---|---|---|---|---|
| Control | 94.045 | 74.374 | 77.449 | 81.956 | 8.64 |
| LPS | 509.043 | >525 | >525 | 519.681 | 7.52 |
| Compound 17ya | 145.157 | 150.069 | 147.179 | 147.468 | 2.02 |

TABLE 3-continued

| IL-6 | | | | | |
|---|---|---|---|---|---|
| | 1 | 2 | 3 | Average | Std Deviation |
| Dex 10 nM | 99.55 | 73.64 | 72.76 | 81.983 | 12.43 |
| LPS | 427.087 | 443.044 | 443.044 | 437.725 | |
| Compound 17ya | 63.201 | 68.113 | 65.223 | 65.512 | |
| Dex 10 nM | 17.594 | −8.316 | −9.196 | 0.0273 | |

TABLE 4

| CXCL-1/KC | | | | | |
|---|---|---|---|---|---|
| | 1 | 2 | 3 | Average | Std Deviation |
| Control | 115.225 | 116.778 | 120.93 | 117.644 | 2.408 |
| LPS | 444.349 | 454.798 | 457.571 | 452.239 | 5.693 |
| Compound 17ya | 125.095 | 136.616 | 132.153 | 131.288 | 4.743 |
| Dex 10 nM | 251.054 | 249.929 | 260.08 | 253.688 | 4.543 |
| LPS | 326.704 | 337.154 | 339.927 | 334.595 | |
| Compound 17ya | 7.451 | 18.192 | 14.509 | 13.644 | |
| Dex 10 nM | 133.410 | 132.285 | 142.436 | 136.043 | |

TABLE 5

| IL-1β | | | | | |
|---|---|---|---|---|---|
| | 1 | 2 | 3 | Average | Std Deviation |
| Control | 6.567 | 7.237 | 6.345 | 6.72 | 0.38 |
| LPS | 29.327 | 30.094 | 29.838 | 29.75 | 0.32 |
| Compound 17ya | 6.567 | 8.823 | 7.013 | 7.47 | 0.98 |
| Dex 10 nM | 4.812 | 4.382 | 3.956 | 4.38 | 0.35 |
| LPS | 22.611 | 23.378 | 23.122 | 23.037 | |
| Compound 17ya | −0.149 | 2.107 | 0.297 | 0.751 | |
| Dex 10 nM | −1.904 | −2.334 | −2.760 | −2.333 | |

TABLE 6

| IL-1α | | | | | |
|---|---|---|---|---|---|
| | 1 | 2 | 3 | Average | Std Deviation |
| Control | 11.628 | 40.388 | 47.982 | 33.333 | 15.658 |
| LPS | 74.83 | 79.509 | 88.751 | 81.030 | 5.784 |
| Compound 17ya | 18.78 | 19.705 | 28.76 | 22.415 | 4.502 |
| Dex 10 nM | 22.962 | 30.814 | 37.012 | 30.266 | 5.753 |
| LPS | 41.497 | 46.176 | 55.418 | 47.697 | |
| Compound 17ya | −14.553 | −13.628 | −4.573 | −10.918 | |
| Dex 10 nM | −10.371 | −2.519 | 3.688 | −3.067 | |

TABLE 7

| | TNF-α | IL-1β | IL-1α | IL-6 | KC |
|---|---|---|---|---|---|
| Compound 17ya | 31% | 97% | 123% | 85% | 96% |
| Dex 10 nM | 79% | 110% | 106% | 100% | 59% |

Example 3

Splenocyte Model for the Treatment of Inflammation

Introduction: In this study (Example 3), the expression of another of the inflammasome modulators, TNF-α, was investigated in freshly harvested mice splenocytes. TNF-α has been shown to be an activator of the inflammasome reaction. In this study, spleen cells from mice were activated with lipopolysaccharide (LPS). In this study, compound 17ya reduced the expression of TNF-α approximately 40%, a similar magnitude as the known inflammatory modulator, colchicine.

Procedure Splenocyte isolation: Mice spleens were harvested from wild-type C57BL/6 male mice (6-8 weeks old) and splenocytes were collected and lysed with red blood cell (RBC) lysis buffer (Sigma, St. Louis, MO). The single-cell suspensions were collected in the RPMI 1640 medium supplemented with 10% fetal bovine serum (FBS) and kept on ice. Freshly harvested splenocytes were pre-incubated with compound 17ya (10 nM-200 nM) and colchicine (200 nM) for 2 hrs in a 24-well plate followed by lipopolysaccharide (LPS) (5 μg/mL) stimulation overnight (20 hrs) at 37° C. in 5% $CO_2$.

Flow cytometry analysis: Intracellular cell antigen staining for single color FACS analysis was performed using Cyto-Fast Fix/Perm Buffer Set (Catalog #42683, BioLegend, CA, USA) with manufacture's protocol. The following antibodies were used for staining: APC-conjugated anti-TNF-α (BioLegend, Clone MP6-XT22, San Diego, CA) and PE-conjugated anti-caspase-1(D3) (Santa Cruz Biotechnology, sc-392736, lot #K0320, Santa Cruz, CA).

Figure 2A:
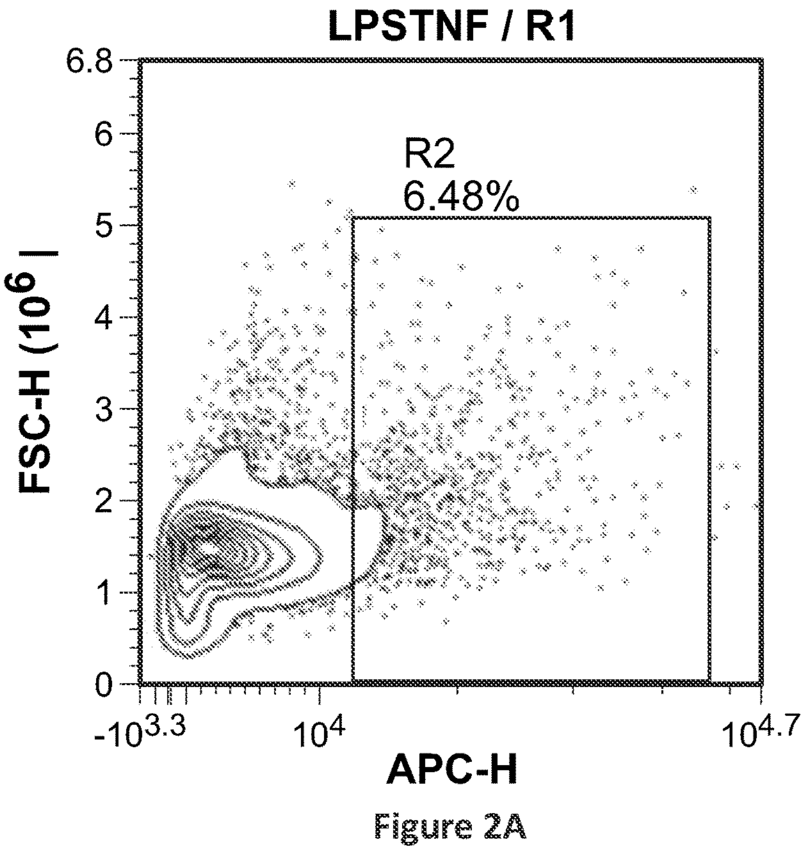
FIGS. 2A-2F illustrate the flow cytometry data of splenocytes pre-incubated with Compound 17ya (10 nM-200 nM) and colchicine (200 nM) and a control.
Figure 2B:
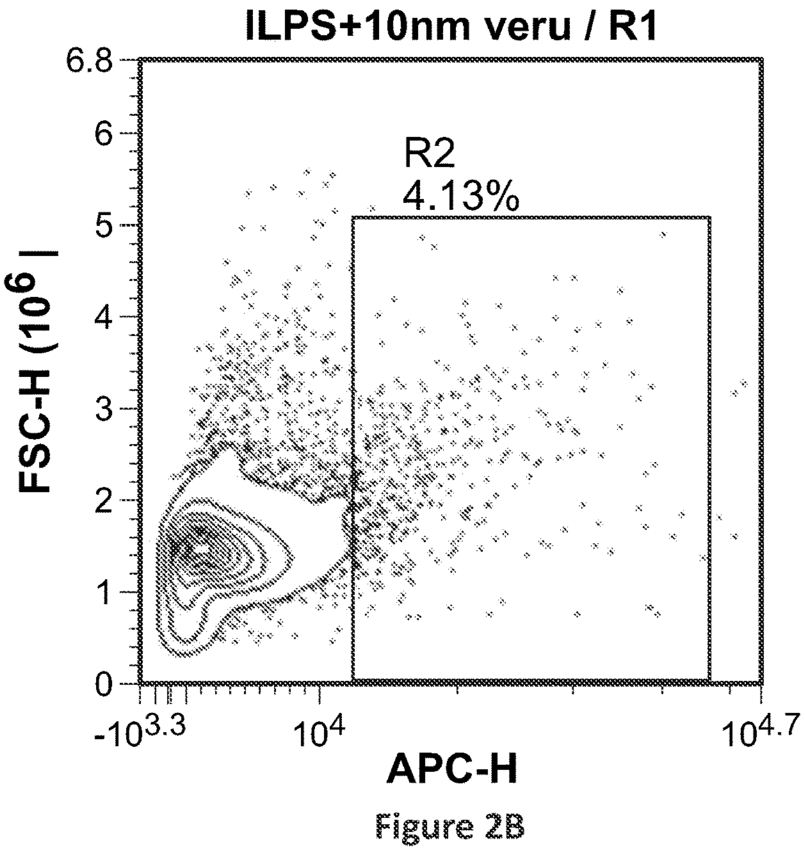
Figure 2C:
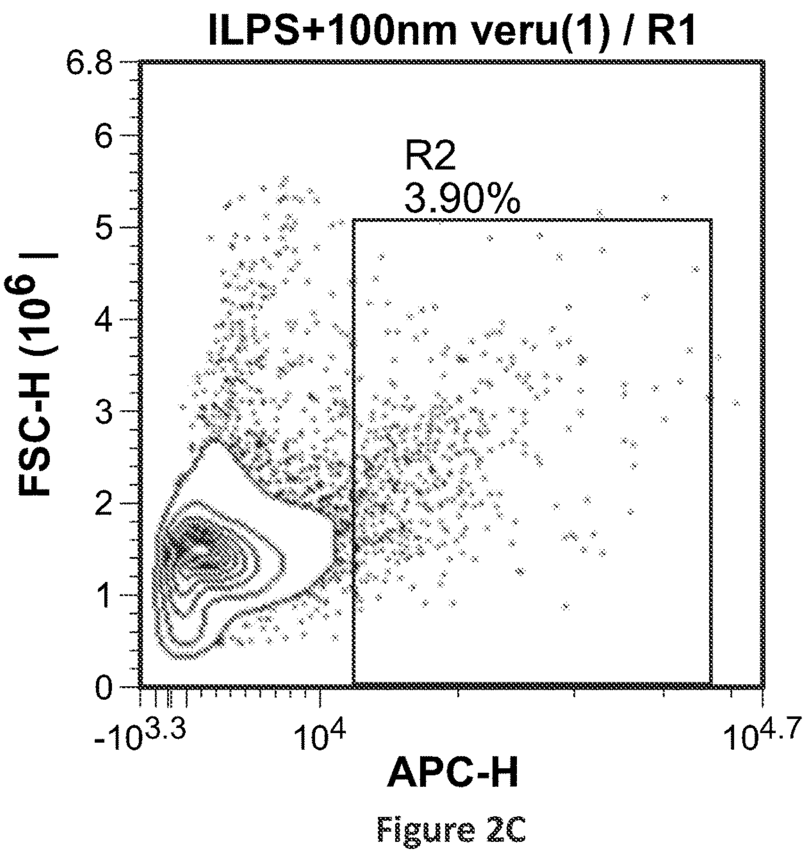
Figure 2D:
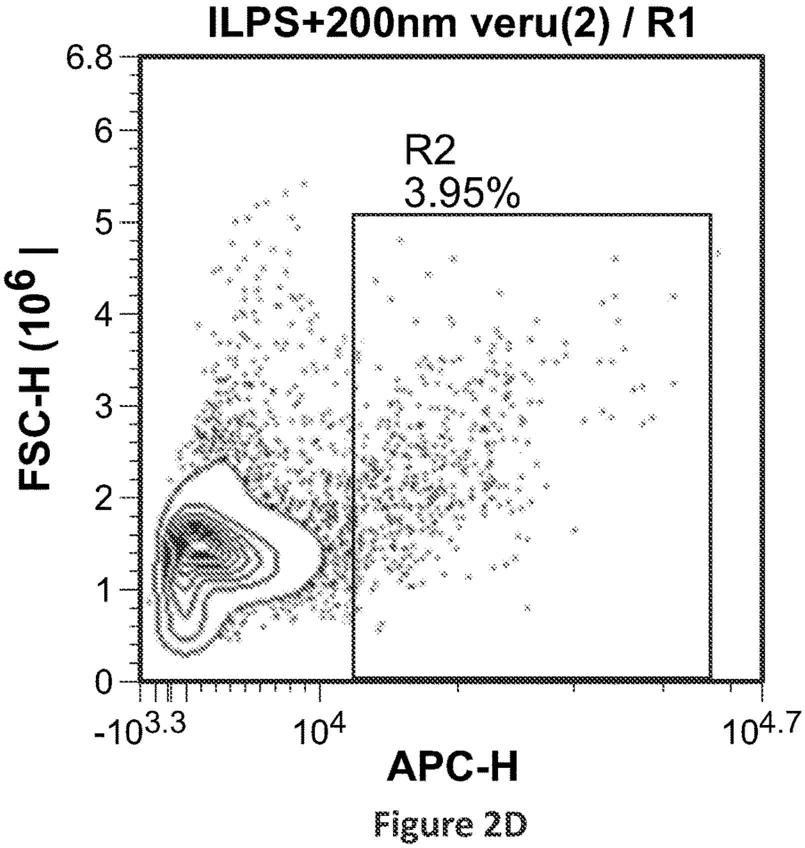
Figure 2E:
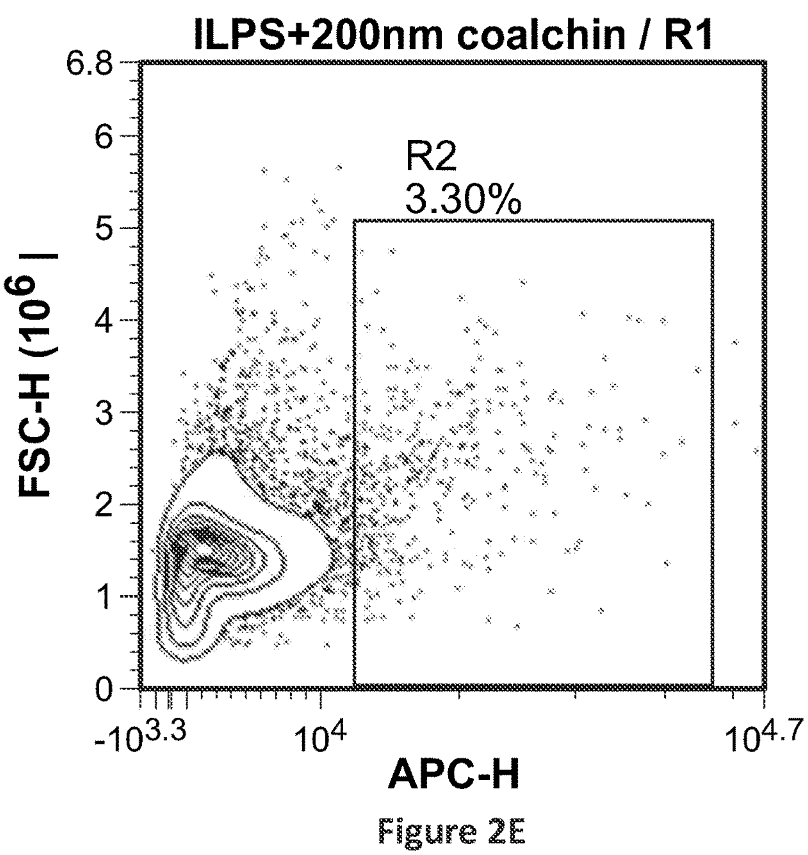
Figure 2F:
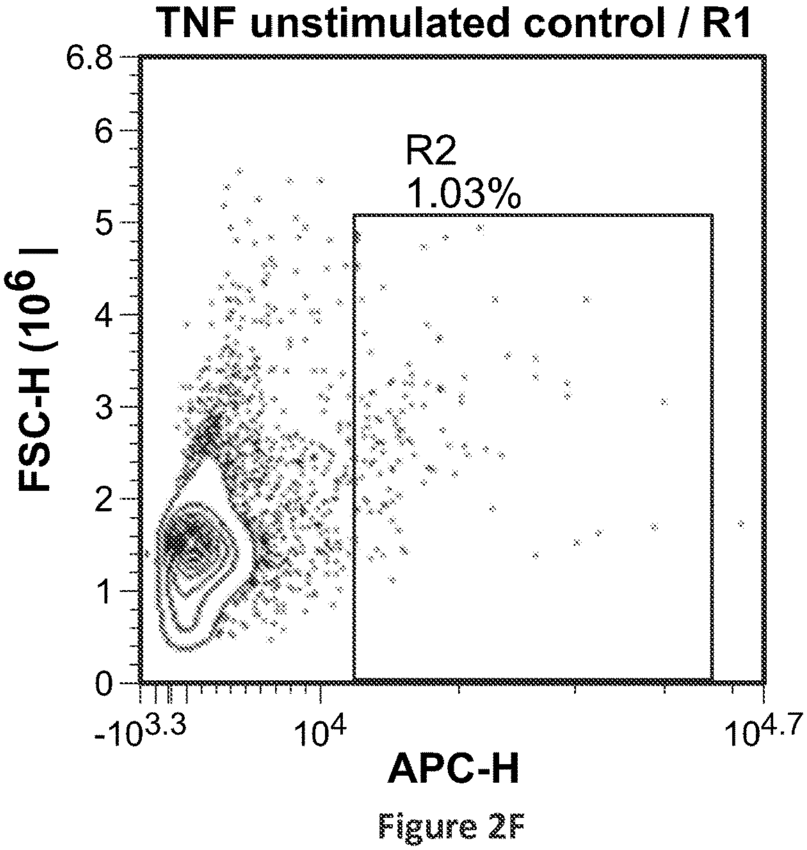

Briefly, cells were washed two times with FACS (PBS containing 1% serum FBS) staining buffer and fully re-suspended in Cyto-Fast Fix/Perm Buffer for 20 min. Then the cells were washed again for two times with Cyto-Fast Perm wash solution and subsequently stained with recommended dilutions of intracellular antibodies for 30 min at room temperature in the dark. After staining, the cells were washed twice in FACS staining buffer, before they were resuspended in FACS staining buffer and analyzed using a NovoCyte flow cytometer (Agilent, Santa Clara, CA). The results of the flow cytometry are illustrated in FIGS. 2A-2F. FIG. 2A illustrates the flow cytometry of splenocytes incubated with LPS. FIG. 2B illustrates the flow cytometry of splenocytes incubated with LPS and Compound 17ya (10 nM). FIG. 2C illustrates the flow cytometry of splenocytes incubated with LPS and Compound 17ya (100 nM). FIG. 2D illustrates the flow cytometry of splenocytes incubated with LPS and Compound 17ya (200 nM). FIG. 2E illustrates the flow cytometry of splenocytes incubated with LPS and Colchicine (200 nM). FIG. 2F illustrates the flow cytometry of splenocytes that were unstimulated (control).

Unstimulated spleen cells had 1.03% expressing TNF-α, while LPS stimulated cells showed a population of 648% that express TNF-α, confirming the stimulation effects of LPS. Preincubation of Compound 17ya decreased TNF-α, production from 6.48% to 4.13% (10 nM), 3.90% (100 nM), and 3.95% (200 nM). The ability of Compound 17ya to reduce TNF-α is comparable with that of colchicine which reduced TNF-α to 3.30% at 200 nM.

Example 4

ELISA Assay to Determine IL-1β in THP-1 Cells

Introduction: A series of experiments examined the ability of compounds of this invention such as compound 17ya to inhibit the inflammasome reaction. The key experiment here is the IL-1β study performed in THP-1 cells (Example 4). These cells are human derived and are designed to study the signals involved in inflammasome activation. To become susceptible to inflammasome inducers, these cells must be induced by stimuli which in this case was phorbol 12-myristate acetate (PMA). Colchicine is an important comparator in these studies since colchicine is known to be an anti-inflammatory compound. Colchicine prevents microtubule assembly and thereby disrupts inflammasome activation, microtubule-based inflammatory cell chemotaxis, generation of leukotrienes and cytokines, and phagocytosis. Colchicine is also utilized clinically for this application.

IL-1β is one of the key modulators of inflammation and a direct readout of the inflammasome complex. Specifically, the NLRP3 inflammasome. In this study, Applicants demonstrated that THP-1 cells that are stimulated by the pro-inflammatory compound, nigericin, produce more IL-1β, than the untreated cells. Microtubule disruptors compound 17ya (labeled as Veru) and colchicine both dose-dependently (partially) suppressed the IL-1β levels induced by nigericin. Further, in comparison to colchicine, compound 17ya had a much greater effect (higher efficacy and potency) in inhibiting IL-1β. Again, in this model, the secretion of IL-1β is an indicator of the inflammasome reaction and therefore the reduction in expression is indicative of an inhibition of the inflammasome reaction. Given these data, it is expected that compounds of the invention would work to treat patients with a wide variety of diseases and conditions with an inflammatory component as described herein and further as known by the skilled artisan.

Procedures: Single-cell suspensions of PMA-differentiated THP-1 cells were collected in the RPMI 1640 medium supplemented with 10% fetal bovine serum (FBS) and kept on ice. PMA-differentiated THP-1 cells were pre-incubated with increasing doses of Compound 17ya (40 nM-5 μM) or Colchicine (1-10 μM) for 1 hr, and then further stimulated by nigericin (20 μM) for 1 hr.

Concentrations of IL-1β in culture supernatant. PMA-differentiated THP-1 cells (100 nM PMA, 24 hr) were pretreated with Compound 17ya (40 nM to 5 μM) or Colchicine (1 and 10 and then nigericin as described above. IL-1β level was assessed by enzyme-linked immunosorbent assay (ELISA) kit for human IL-1β (R&D systems) (****P<0.0001, Ordinary one-way ANOVA, Prism 9).

Figure 3A:
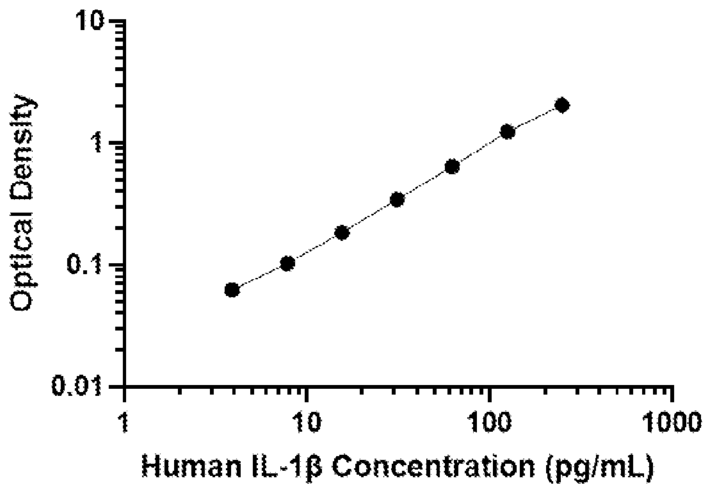
FIGS. 3A and 3B illustrate the ELISA assay results to determine IL-1β in THP-1 cells.
Figure 3B:
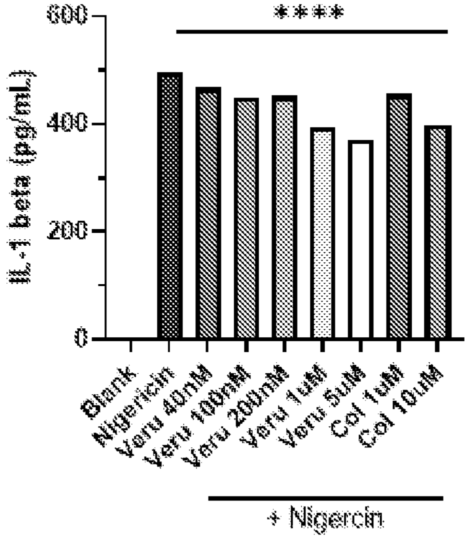

The standard curve for the ELISA assay shows the expected linear response as illustrated in FIG. 3A. The results of the ELISA assay are illustrated in FIG. 3B. Both Compound 17ya and colchicine significantly suppressed IL-1β secretion in response to nigericin stimulation in a dose dependent manner. Moreover, Compound 17ya inhibited the IL-1β level to a more prominent level (greater efficacy and greater potency) compared with that of colchicine, demonstrating statistically significant anti-inflammatory activity in a human derived cell line induced with PMA to be monocytic (http://www.atcc.org/products/tib-202). This data supports that compounds of this invention can be used to suppress IL-1β, a pro-inflammatory cytokine derived from the inflammasome, which is known to be involved in the pathology of many inflammatory diseases and disorders.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating inflammation in a subject in need thereof by administering to the subject a formulation having a therapeutically effective amount of a compound of Formula (I):

(I)

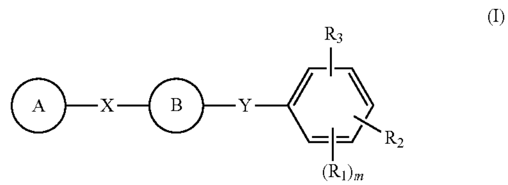

wherein

A is phenyl, indolyl, or indazolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

B is an imidazole or benzimidazole, optionally substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2CN$, hydroxyl, or $NO_2$;

$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

X is a bond or NH;

Y is a bond or —C═O; and m is 1-3, or a pharmaceutically acceptable salt, hydrate, or stereoisomer thereof wherein the inflammation is caused by or associated with SARS-CoV, MERS-CoV, or SARS-CoV-2.

2. The method of treating inflammation according to claim 1, wherein A is phenyl or indolyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

B is an imidazole, optionally substituted with at least one of $(C_1-C_4)$alkyl;

$R_1$, $R_2$ and $R_3$ are independently at least one of hydrogen, $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, $OC(O)CF_3$, —$OCH_2Ph$, —NHCO—$(C_1-C_4)$alkyl, COOH, —C(O)Ph, C(O)O—$(C_1-C_4)$alkyl, C(O)H, —$C(O)NH_2$ or $NO_2$;

X is a bond or NH;

Y is —C═O; and m is 1-3, or a pharmaceutically acceptable salt, hydrate, or stereoisomer thereof.

3. The method of treating inflammation according to claim 1, wherein A is phenyl, optionally substituted with at least one of $(C_1-C_4)$alkyl, halo$(C_1-C_4)$alkyl, O—$(C_1-C_4)$alkyl, O—$(C_1-C_4)$haloalkyl, $(C_1-C_4)$alkylamino, amino$(C_1-C_4)$alkyl, F, Cl, Br, I, CN, —$CH_2CN$, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

B is an imidazole, optionally substituted with at least one of ($C_1$-$C_4$)alkyl;

$R_1$, $R_2$ and $R_3$ are independently at least one of hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

X is a bond or NH;

Y is —C═O; and m is 1-3, or a pharmaceutically acceptable salt, hydrate, or stereoisomer thereof.

4. The method of treating inflammation according to claim 1, wherein A is indolyl, optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

B is an imidazole, optionally substituted with at least one of ($C_1$-$C_4$)alkyl;

$R_1$, $R_2$ and $R_3$ are independently at least one of hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

X is a bond or NH;

Y is —C═O; and m is 1-3, or a pharmaceutically acceptable salt, hydrate, or stereoisomer thereof.

5. The method of treating inflammation according to claim 1, wherein A is indolyl, optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

B is an imidazole, optionally substituted with at least one of ($C_1$-$C_4$)alkyl;

$R_1$, $R_2$ and $R_3$ are independently at least one of hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

X is a bond;

Y is —C═O; and m is 1-3, or a pharmaceutically acceptable salt, hydrate, or stereoisomer thereof.

6. The method of treating inflammation according to claim 1, wherein, the compound has a structure of Formula VII:

(VII)

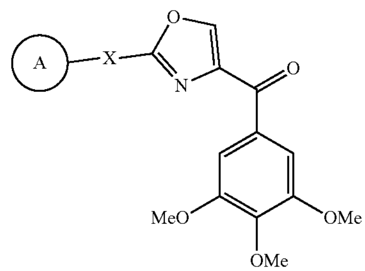

wherein

X is a bond or NH;

Q is NH and

A is a phenyl, indolyl, or indazolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, or stereoisomer thereof.

7. The method of treating inflammation according to claim 6, wherein X is a bond.

8. The method of treating inflammation according to claim 6, wherein X is NH.

9. The method of treating inflammation according to claim 6, wherein X is a bond; Q is NH; and A is an indolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, or stereoisomer thereof.

10. The method of treating inflammation according to claim 1, wherein, the compound has a structure of Formula VII(c):

VII(c)

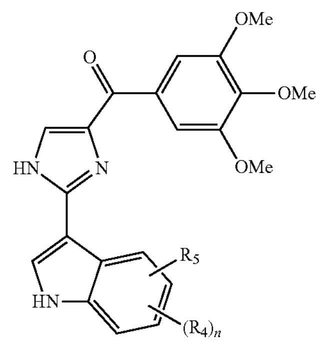

wherein $R_4$ and $R_5$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; and n is 1-4; or a pharmaceutically acceptable salt, hydrate, or stereoisomer thereof.

11. A method of treating inflammation in a subject in need thereof by administering to the subject a formulation having a therapeutically effective amount of a compound 17ya represented as:

(17ya)

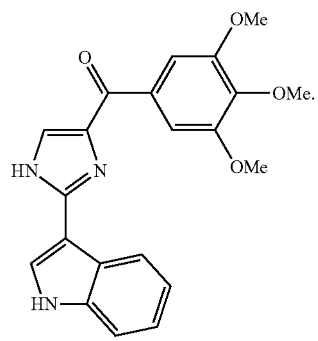

12. The method of treating inflammation according to claim 1, wherein the inflammation is responsive to suppression of IL-1β.

13. The method of treating inflammation according to claim 1, wherein the inflammation is responsive to suppression of TNF-α.

14. The method of treating inflammation according to claim 1, wherein the subject with SARS-CoV-2 infection is at high risk for acute respiratory distress syndrome (ARDS) or severe acute respiratory syndrome (SARS).

15. The method of treating inflammation according to claim 14, wherein the method reduces mortality.

16. The method of treating inflammation according to claim 14, wherein the method reduces morbidity.

17. The method of treating inflammation according to claim 1 further comprising a second therapy.

18. The method of treating inflammation according to claim 1, wherein the compound is administered in an amount of about 1 to about 100 mg.

19. The method of treating inflammation according to claim 1, wherein the compound is administered in an amount of about 4 mg to about 90 mg.

20. The method of treating inflammation according to claim 1, wherein the compound is administered in an amount of about 4 mg to about 45 mg.

21. The method of treating inflammation according to claim 1 further comprising a pharmaceutically acceptable excipient.

* * * * *